(12) United States Patent
Kapeller-Libermann

(10) Patent No.: US 6,630,335 B1
(45) Date of Patent: Oct. 7, 2003

(54) 14171 PROTEIN KINASE, A NOVEL HUMAN PROTEIN KINASE AND USES THEREOF

(75) Inventor: Rosana Kapeller-Libermann, Chestnut Hill, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/781,882

(22) Filed: Feb. 12, 2001

Related U.S. Application Data

(60) Provisional application No. 60/182,096, filed on Feb. 11, 2000.

(51) Int. Cl.[7] .............................. C12N 9/12; C12N 1/20; C12N 15/00; C12N 5/00; C12Q 1/68
(52) U.S. Cl. .................... 435/194; 435/320.1; 435/325; 435/252.3; 435/6; 536/23.2
(58) Field of Search ............................... 435/194, 252.3, 435/325, 320.1, 6; 536/23.2

(56) References Cited

FOREIGN PATENT DOCUMENTS

| EP | 1074617 A2 | 2/2001 |
|---|---|---|
| WO | 99/04265 * | 1/1999 |
| WO | WO 99/55865 A1 | 11/1999 |
| WO | WO 00/8177 A2 | 2/2000 |
| WO | WO 00/08178 A2 | 2/2000 |
| WO | WO 01/38503 A2 | 5/2001 |
| WO | WO 01/57188 A2 | 8/2001 |
| WO | WO 01/81363 A1 | 11/2001 |

OTHER PUBLICATIONS

Holland, Pamela M. et al., "RIP4 Is an Ankyrin Repeat–Containing Kinase Essential for Keratinocyte Differentiation" *Current Biology* vol. 12, (Aug. 20, 2002), pp. 1424–1428.

Bähr, Corinna et al., "DIK, A Novel Protein Kinase that Interacts with Protein Co" *The Journal of Biological Chemistry* vol. 275, (Nov. 17, 2000), pp. 36350–36357.

Hattori, M. et al., "The DNA Sequence of Human Chromosome 21" *Nature* vol. 405 (May 18, 2000), pp. 311–319.

Bloecker, H. et al., "Homo sapiens mRNA; cDNA DKFZp434B2328 (from clone DKFZp434B2328); partial cds." Feb. 18, 2000 (sequence) GenBank [online] Bethesda, MD, USA: National Center for Biotechnology Information [retrieved on Sep. 5, 2002]. Retrieved from the Internet: <URL: http://www.ncbi.nlm.nih.gov/>. GenBank Accession No. AL137448.

Thome, M. et al., Identification of CARDIAK, A RIP–like Kinase that Associated with Caspase–1, Current Biology, vol. 8(15) 1988.

* cited by examiner

*Primary Examiner*—M. Monshipouri
(74) *Attorney, Agent, or Firm*—Millennium Pharmaceuticals, Inc.

(57) ABSTRACT

The invention relates to a novel kinase nucleic acid sequence and protein. Also provided are vectors, host cells, and recombinant methods for making and using the novel molecules.

15 Claims, 13 Drawing Sheets

FIG. 1A

| FIG. 1A-1 | FIG. 1A-2 |

```
Input file Fbh14171b.seq; Output File 14171.trans
Sequence Length 3860

M   E   G   D   G   G   T   P   W   A   L   A   L   L   R              15
CCACGCGTCCGGCCGCG  ATG GAG GGC GAC GGG ACC CCA TGG GCC CTG GCG CTG CTG CGC              61
                                                                                         45

T   F   D   A   G   E   F   T   G   W   E   K   V   G   S   G   F   G   Q              35
ACC TTC GAC GCG GGC GAG TTC ACG GGC TGG GAG AAG GTG GGC TCG GGC TTC GGG CAG             121
                                                                                        105

V   Y   K   V   R   H   V   H   W   K   T   W   L   A   I   K   C   S   P   S          55
GTG TAC AAG GTG CGC CAT GTC CAC TGG AAG ACC TGG CTG GCC ATC AAG TGC TCG CCC AGC         181
                                                                                        165

L   H   V   D   D   R   E   M   R   M   E   L   E   E   A   K   K   M   E   M          75
CTG CAC GTC GAC GAC AGG GAG ATG CGC ATG GAG CTT TTG GAA GAA GCC AAG AAG ATG GAG ATG     241
                                                                                        225

A   K   F   R   Y   I   L   P   V   Y   G   I   C   R   E   P   V   G   L   V          95
GCC AAG TTT CGC TAC ATC CTG CCT GTG TAT GGC ATC TGC CGC GAA CCT GTC GGC CTG GTC         301
                                                                                        285

M   E   Y   M   E   T   G   S   L   E   K   L   A   S   E   P   L   P   W             115
ATG GAG TAC ATG GAG ACG GGC TCC CTG GAA AAG CTG GCT CTG TCG GAG CCA TTG CCA TGG         361
                                                                                        345

D   L   R   F   R   I   I   H   E   T   A   V   G   M   N   F   L   H   C   M         135
GAT CTC CGG TTC CGA ATC ATC CAC GAG ACG GCG GTG GGC ATG AAC TTC CTG CAC TGC ATG         421
                                                                                        405
```

| FIG. 1B-1 | FIG. 1B-2 | FIG. 1B-3 |

FIG. 1B-1

```
                                                                          1185
S   V   D   S   A   F   G   L   T   T   R   R   P   E   E   A   C   G   H   R
TCG GTG GAC TCC GCC TTC TCT TCC AGA GGA TCA CTG TCC TTT GAG CGG GAA CCT
TCA ACC AGC GAT CTG GGT CTG ACC ACA CGT AGA CCA GAA GAA GCT TGT GGA TGC CAT CGT
                                                                          415
                                                                          1245
V   R   D   T   S   K   L   M   I   K   L   Q   D   V   D   L   A   L
GTC CGG GAC ACC AGC AAA CTG ATG ATC AAG CTG CAG GAC GTG GAC CTG GCA CTG
                                                                          435
                                                                          1305
D   S   G   A   S   L   H   L   A   V   E   Q   G   E   E   C   A   K
GAC AGC GGT GCC AGC CTG CAC CTG GCG GTG GAG CAA GGG GAG GAG TGC GCC AAG
                                                                          455
                                                                          1365
                                                                          1381
```

| | | | | | | | | | | | | |
|---|---|---|---|---|---|---|---|---|---|---|---|---|
| W TGG | L CTG | L CTC | N AAC | A GCC | N AAT | P CCC | N AAC | L CTG | S AGC | N AAC | R CGT | R AGG | G GGC | S TCC | T ACC | P CCG | L TTG | 475 1425 |
| H CAC | M ATG | A GCC | V GTG | E GAG | R AGG | R AGG | V GTG | G GGT | V GTC | E GAG | L CTC | L CTG | L CTG | A GCA | R CGG | K AAG | I ATC | 495 1485 |
| S AGT | N AAC | A GCC | S TCT | D GAT | T ACA | W TGG | D GAC | T ACA | A GCA | L CTC | H CAC | F TTT | A GCA | A GCC | Q CAG | N AAC | G GGG | 515 1545 |
| D GAT | E GAG | S TCT | R CGG | M ATG | D GAT | L CTG | R CGG | L CTG | V GTG | K AAG | N AAC | A GCC | S TCG | V GTC | E GAG | D GAC | F TTT | 535 1605 |
| E GAG | G GGC | R CGG | T ACA | P CCC | Q CAG | V GTG | H CAC | V GTG | C TGC | Q CAG | H CAC | G GGG | N AAT | E GAG | Q CAG | V GTG | R I CGC ATC | 555 1665 |
| L CTG | L CTG | R CGC | R CGA | G GGC | Q CAG | V GTG | D GAC | L CTG | V GTG | L CTG | D GAC | A GCC | W TGG | K AAG | L CTG | P CCA | H CAC | 575 1725 |
| Y TAC | A GCT | W TGG | Q CAG | A GCC | H CAC | I ATC | L CTG | I ATC | A GCC | A GCC | L CTG | A GCC | K AAG | A GCC | P CCG | G GGG | V GTG | 595 1785 |
| S AGT | N AAC | A GCC | V GTG | P CCC | Q CAG | H CAC | V GTC | P CCC | R AGG | G GGG | D GAC | L CTG | H CAC | V GTC | A GCA

| | | | | | | | | | | | |
|---|---|---|---|---|---|---|---|---|---|---|---|
| L<br>CTG | A<br>GCT | A<br>GCC | R<br>CGC | N<br>AAC | G<br>GGA | H<br>CAC | L<br>CTG | A<br>GCC | T<br>ACT | V<br>GTC | K<br>AAG | L<br>CTG | L<br>CTT | V<br>GTC | E<br>GAG | E<br>GAG | K<br>AAG | A<br>GCC | D<br>GAT | 695<br>2085 | 2061 |
| V<br>GTG | L<br>CTG | A<br>GCC | R<br>CGG | G<br>GGA | P<br>CCC | L<br>CTG | N<br>AAC | Q<br>CAG | T<br>ACG | A<br>GCG | L<br>CTG | H<br>CAC | L<br>CTG | A<br>GCT | A<br>GCC | A<br>GCC | H<br>CAC | G<br>GGG | H<br>CAC | 715<br>2145 | 2081 |
| S<br>TCG | E<br>GAG | V<br>GTG | V<br>GTG | E<br>GAG | P<br>CCC | L<br>CTG | E<br>GAG | L<br>TTG | V<br>GTC | S<br>AGC | A<br>GCC | A<br>GCC | D<br>GAT | V<br>GTC | I<br>ATT | L<br>CTG | D<br>GAC | F<br>TTC | D<br>GAC | E<br>GAG | G<br>GGG | 735<br>2205 | 2141 |
| L<br>CTC | A<br>GCG | H<br>CAC | A<br>GCC | H<br>CAC | L<br>CTG | I<br>ATC | N<br>AAC | A<br>GCC | Q<br>CAG | R<br>CGG | H<br>CAC | A<br>GCA | Q<br>CAG | T<br>ACG | V<br>GTG | E<br>GAG | T<br>ACT | L<br>CTG | L<br>CTC | 755<br>2265 | 2201 |
| R<br>AGG | H<br>CAT | G<br>GGG | A<br>GCC | H<br>CAC | I<br>ATC | N<br>AAC | L<br>CTG | S<br>AGC | L<br>CTC | K<br>AAG | F<br>TTC | Q<br>CAG | G<br>GGC | G<br>GGC | H<br>CAT | G<br>GGC | P<br>CCC | A<br>GCC | 775<br>2325 | 2261 |
| A<br>GCC | T<br>ACA | L<br>CTC | L<br>CTG | R<br>CGG | R<br>CGA | S<br>AGC | K<br>AAG | T<br>ACC | \*<br>TAG | | | | | | | | | | | 2355 |

```
CTGGCTGCCTGCGGAGACCGGGGGTCCACGTGGGGCTCTCTGTCCTGTGTCCTCGTGGGATGGAACGATCCTG
CGTGGGGCCCCGTTGTGGCTTACCTAAATGTTAACCAAGCAGAGGTGACATGGTGCCATCAGGAGGCGGCTGCTGCTGA
CCGGAGTGTCCCCTCCAGTGAAGCTGGCTCAGTGCACATGCCCGCTCCATCATGATCTAGGCACCTGCTGTCTGAA
GGGACCGTGGGTCAGAATCATTCGTTGTGCTCCTAATGGGTCGCTGAGGCTGGTCTCTCAGTGATGAAGCCCAGGCG
TGGAAGCATCCACTCTCCCTGAGGCGAGCCACCTTGGGTTGCTGGAGCTCACCAGTCTTGAGGGAGGTGCAGGGAAA
CTGTGTTTTTTATCTTCATACATGACGGTGGGCAGAGAGCCCTGTCTTAAAGTTTCCATGGAATTGTTTTATAAAATAT
CTTAAGAGATGAATACCTTATCAGCTGTTGCTTGAAACCTGTTAAAATGTTCATAACATTGGATAGTCTAGTCTCTAA
ATGATGGCTAAGTAGTGGGGTTGGCTTTGAAAACAATGTTTATGCAACAAGGAACGAATGGTAGCAGCCAGCTTTGCG
GGGCGTATGTGTGGCCAGCTCTTAACCATTCCAGTCTATTACTTGGGTGAGTCCTTGTGGCAACTCTAGAGCCACACGTGCC
CACATGTACTAGCTGCCGTTCGTTCTCGTTGCCTAAGATGTTTGGCAGCTGCGAGGCGAGCCCCTCAGGTGCGCTGAGTCATT
AAAAAATTCCCCTTTGTAACCTCAGTGCTGTGTTTTATCTCCACACGCAGTGAAGATAAAATTACATAGTATTACCTAGACATA
GAAGAGGTGCAGGAGAAGCTGTGTTTTATCTCCACACGCAGTGAAGATAAAATTACATAGTATTACCTAGACATA
GACAGTATTACCTAGTAGAGATGCACTGCTCACCTGCCACCCTTCCCAGCTCTCATTTTGTTAGGTGATTGGGATAGGG
ATAGTGTTTTGGGGTATGGGGGAGTGTTTCTGACCTGTTTGCAGACGTGCCTCCCGCACCTCAGCAGTTTGGGGTGTG
GCCCCAGGGCGGTTCTTGGATGTAAAAGATGTGGCCATCTAGCCTCGTAACTTCACTGTGTCCCATAGGGTG
CCTTCTGAATACTGTTATTAGAATAAGTTTGTGCAGAACGTGACCCTGCCGTGCAAACATGTACCGTGCCTGGTATAT
GATAGAGATTGATATTAATGTACCATGTATGTTAATGTGAATCTGTGGCAGGATACTTTCCATGCCAGGAAATATCC
AAGCTGTGAAACTGGCTATGTTTAATATGCCTCATTGCCTTTACTGTTGTGTGGACTGCGTGAGGGACAAGAAGT
TCCATTTGATGTCAATAAGCAAAGTACTTGCCTACTTTTTTGAANCTGAAAAAAAAAAAAGG
```

FIG. 1C

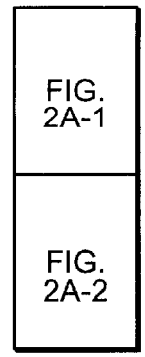

FIG. 2A

Prosite Pattern Matches for 14171
Prosite version: Release 12.2 of February 1995

```
>PS00001|PDOC00001|ASN_GLYCOSYLATION
N-glycosylation site.

Query:      465     NLSN    468
Query:      527     NASV    530
Query:      703     NQTA    706

>PS00002|PDOC00002|GLYCOSAMINOGLYCAN
Glycosaminoglycan attachment site.
        RU      Additional rules:
        RU      There must be at least two acidic
                amino acids (Glu or Asp)from -2 to
        RU      -4 relative to the serine.

Query:      365     SGSG    368

>PS00004|PDOC00004|CAMP_PHOSPHO_SITE cAMP- and
cGMP-dependent protein kinase phosphorylation
site.

Query:      319     KRAS    322
Query:      369     KRLS    372
Query:      469     RRGS    472
Query:      493     RKIS    496
```

FIG. 2A-1

>PS00005|PDOC00005|PKC_PHOSPHO_SITE
Protein kinase C phosphorylation site.

```
Query:       218     TQK     220
Query:       367     SGK     369
Query:       382     SSR     384
Query:       402     TTR     404
Query:       419     TSK     421
Query:       467     SNR     469
Query:       519     STR     521
Query:       652     TAR     654
Query:       685     TVK     687
Query:       765     SLK     767
```

>PS00006|PDOC00006|CK2_PHOSPHO_SITE
Casein kinase II phosphorylation site.

```
Query:       23      TGWE    26
Query:       202     TKHD    205
Query:       275     TFQE    278
Query:       281     SETE    284
Query:       297     TAHD    300
Query:       305     SPPE    308
Query:       331     SLSE    334
Query:       337     SQLD    340
Query:       356     SSSE    359
Query:       375     SSVD    378
Query:       396     STSD    399
Query:       529     SVNE    532
```

FIG. 2A-2

>PS00008|PDOC00008|MYRISTYL N-myristoylation site.

| Query: | 6 | GTPWAL | 11 |
| --- | --- | --- | --- |
| Query: | 163 | GLAKCN | 168 |
| Query: | 169 | GLSHSH | 174 |
| Query: | 180 | GLFGTI | 185 |
| Query: | 342 | GVSQAV | 347 |
| Query: | 449 | GQEECA | 454 |
| Query: | 560 | GVDVSL | 565 |
| Query: | 594 | GVSVNA | 599 |
| Query: | 758 | GAHINL | 763 |

>PS00009|PDOC00009|AMIDATION Amidation site.
| Query: | 367 | SGKR | 370 |
| --- | --- | --- | --- |

>PS00107|PDOC00100|PROTEIN_KINASE_ATP Protein kinases ATP-binding region signature.

| Query: | 28 | VGSGGFGQV | 36 |
| --- | --- | --- | --- |

>PS00108|PDOC00100|PROTEIN_KINASE_ST Serine/Threonine protein kinases active-site signature.

| Query: | 139 | LLHLDLKPANILL | 151 |
| --- | --- | --- | --- |

>PS00141|PDOC00128|ASP_PROTEASE Eukaryotic and viral aspartyl proteases active site.

| Query: | 433 | LALDSGASLLHL | 444 |
| --- | --- | --- | --- |

FIG. 2B

```
       *->yelleklGeGsfGkVykakhk.tgkivAvKilk......kesls.lr
       ++  ek+G+G+fG+Vyk++h++ +   A+K+ ++  +   +++e+++ 1
14171 22  FTGWEKVGSGGFGQVYKVRHVhWKTWLAIKCSPslhvddRERMEllE 68

EiqilkrlshHpNIvrllgvfedtddhlylvmEymegGdLfdylrrngpls
          E++ + + + +I+ ++g+++      +++ lvmEyme G+L ++l ++ 1+
14171 69  EAKKMEMAKFRYILPVYGICR---EPVGLVMEYMETGSLEKLLASEP-LP 114 ekeakkialQilrGleYLHsng..ivHRDLKpeNILldengtvKiaDFGL
          ++   +i+++++ G+++LH +  ++ +H DLKp+NIlld + +vKi+DFGL
14171 115 WDLRFRIIHETAVGMNFLHCMAppLLHLDLKPANILLDAHYHVKISDFGL 164

Arll.......ekLttfvGTpwYmmAPEvileg..rgysskvDvWSlGvi
          A++  + +++++ +  ++ GT+ Y +PE  ++ ++r +++k Dv+S+ ++
14171 165 AKCNglshshdLSMDGLFGTIAYL-PPER--IREksRLFDTKHDVYSFAIV 212

LyElltggplfpgadlpaftggdevdqliifvlklPfsdelpktridple
                                            k Pf de  k+  +++
14171 213 IWGVLTQ------------------------KKPFADE--KNILHIMV 234 elfrikkr......rlplpsncSeelkdLlkkcLnkDPskRpGsatakei<
          +++++ + ++   ++    +p+ cS  l+ L+ +c++ DP Rp   t++ei
14171 235 KVVKGHRPelppvCRARPRACSH-LIRLMQRCWGDPRVRP---TFQEI 279
```

FIG. 6

SEQUENCE LISTING

<160> NUMBER OF SEQ ID NOS: 4

<210> SEQ ID NO 1
<211> LENGTH: 3860
<212> TYPE: DNA
<213> ORGANISM: H. sapiens
<220> FEATURE:
<221> NAME/KEY: CDS
<222> LOCATION: (17)...(2371)
<223> OTHER INFORMATION:
<221> NAME/KEY: misc_feature
<222> LOCATION: (1)...(3860)
<223> OTHER INFORMATION: n = A,T,C or G

<400> SEQUENCE: 1

```
ccacgcgtcc ggcgcg atg gag ggc gac ggc ggg acc cca tgg gcc ctg gcg      52
               Met Glu Gly Asp Gly Gly Thr Pro Trp Ala Leu Ala
                 1               5                  10 ctg ctg cgc acc ttc gac gcg ggc gag ttc acg ggc tgg gag aag gtg       100
Leu Leu Arg Thr Phe Asp Ala Gly Glu Phe Thr Gly Trp Glu Lys Val
         15                  20                  25 ggc tcg ggc ggc ttc ggg cag gtg tac aag gtg cgc cat gtc cac tgg       148
Gly Ser Gly Gly Phe Gly Gln Val Tyr Lys Val Arg His Val His Trp
     30                  35                  40 aag acc tgg ctg gcc atc aag tgc tcg ccc agc ctg cac gtc gac gac       196
Lys Thr Trp Leu Ala Ile Lys Cys Ser Pro Ser Leu His Val Asp Asp
 45                  50                  55                  60 agg gag cgc atg gag ctt ttg gaa gaa gcc aag aag atg gag atg gcc       244
Arg Glu Arg Met Glu Leu Leu Glu Glu Ala Lys Lys Met Glu Met Ala
                 65                  70                  75 aag ttt cgc tac atc ctg cct gtg tat ggc atc tgc cgc gaa cct gtc       292
Lys Phe Arg Tyr Ile Leu Pro Val Tyr Gly Ile Cys Arg Glu Pro Val
             80                  85                  90 ggc ctg gtc atg gag tac atg gag acg ggc tcc ctg gaa aag ctg ctg       340
Gly Leu Val Met Glu Tyr Met Glu Thr Gly Ser Leu Glu Lys Leu Leu
         95                 100                 105 gct tcg gag cca ttg cca tgg gat ctc cgg ttc cga atc atc cac gag       388
Ala Ser Glu Pro Leu Pro Trp Asp Leu Arg Phe Arg Ile Ile His Glu
     110                 115                 120 acg gcg gtg ggc atg aac ttc ctg cac tgc atg gcc ccg cca ctc ctg       436
Thr Ala Val Gly Met Asn Phe Leu His Cys Met Ala Pro Pro Leu Leu
125                 130                 135                 140 cac ctg gac ctc aag ccc gcg aac atc ctg ctg gat gcc cac tac cac       484
His Leu Asp Leu Lys Pro Ala Asn Ile Leu Leu Asp Ala His Tyr His
                 145                 150                 155 gtc aag att tct gat ttt ggt ctg gcc aag tgc aac ggg ctg tcc cac       532
Val Lys Ile Ser Asp Phe Gly Leu Ala Lys Cys Asn Gly Leu Ser His
             160                 165                 170 tcg cat gac ctc agc atg gat ggc ctg ttt ggc aca atc gcc tac ctc       580
Ser His Asp Leu Ser Met Asp Gly Leu Phe Gly Thr Ile Ala Tyr Leu
         175                 180                 185 cct cca gag cgc atc agg gag aag agc cgg ctc ttc gac acc aag cac       628
Pro Pro Glu Arg Ile Arg Glu Lys Ser Arg Leu Phe Asp Thr Lys His
     190                 195                 200 gat gta tac agc ttt gcg atc gtc atc tgg ggc gtg ctc aca cag aag       676
Asp Val Tyr Ser Phe Ala Ile Val Ile Trp Gly Val Leu Thr Gln Lys
205                 210                 215                 220 aag ccg ttt gca gat gag aag aac atc ctg cac atc atg gtg aag gtg       724
Lys Pro Phe Ala Asp Glu Lys Asn Ile Leu His Ile Met Val Lys Val
                 225                 230                 235
```

```
gtg aag ggc cac cgc ccc gag ctg ccg ccc gtg tgc aga gcc cgg ccg         772
Val Lys Gly His Arg Pro Glu Leu Pro Pro Val Cys Arg Ala Arg Pro
            240                 245                 250 cgc gcc tgc agc cac ctg ata cgc ctc atg cag cgg tgc tgg cag ggg         820
Arg Ala Cys Ser His Leu Ile Arg Leu Met Gln Arg Cys Trp Gln Gly
        255                 260                 265 gat ccg cga gtt agg ccc acc ttc caa gaa att act tct gaa acc gag         868
Asp Pro Arg Val Arg Pro Thr Phe Gln Glu Ile Thr Ser Glu Thr Glu
    270                 275                 280 gac ctg tgt gaa aag cct gat gac gaa gtg aaa gaa act gct cat gat         916
Asp Leu Cys Glu Lys Pro Asp Asp Glu Val Lys Glu Thr Ala His Asp
285                 290                 295                 300 ctg gac gtg aaa agc ccc ccg gag ccc agg agc gag gtg gtg cct gcg         964
Leu Asp Val Lys Ser Pro Pro Glu Pro Arg Ser Glu Val Val Pro Ala
                305                 310                 315 agg ctc aag cgg gcc tct gcc ccc acc ttc gat aac gac tac agc ctc        1012
Arg Leu Lys Arg Ala Ser Ala Pro Thr Phe Asp Asn Asp Tyr Ser Leu
            320                 325                 330 tcc gag ctt ctc tca cag ctg gac tct gga gtt tcc cag gct gtc gag        1060
Ser Glu Leu Leu Ser Gln Leu Asp Ser Gly Val Ser Gln Ala Val Glu
        335                 340                 345 ggc ccc gag gag ctc agc cgc agc tcc tct gag tcc aag ctg cca tcg        1108
Gly Pro Glu Glu Leu Ser Arg Ser Ser Ser Glu Ser Lys Leu Pro Ser
    350                 355                 360 tcc ggc agt ggg aag agg ctc tcg ggg gtg tcc tcg gtg gac tcc gcc        1156
Ser Gly Ser Gly Lys Arg Leu Ser Gly Val Ser Ser Val Asp Ser Ala
365                 370                 375                 380 ttc tct tcc aga gga tca ctg tcg ctg tcc ttt gag cgg gaa cct tca        1204
Phe Ser Ser Arg Gly Ser Leu Ser Leu Ser Phe Glu Arg Glu Pro Ser
                385                 390                 395 acc agc gat ctg ggt acc aca aga cgt cca gaa gaa gaa gct tgt gga        1252
Thr Ser Asp Leu Gly Thr Thr Arg Arg Pro Glu Glu Glu Ala Cys Gly
            400                 405                 410 tgc cat cgt gtc cgg gac acc agc aaa ctg atg aag atc ctg cag ccg        1300
Cys His Arg Val Arg Asp Thr Ser Lys Leu Met Lys Ile Leu Gln Pro
        415                 420                 425 cag gac gtg gac ctg gca ctg gac agc ggt gcc agc ctg ctg cac ctg        1348
Gln Asp Val Asp Leu Ala Leu Asp Ser Gly Ala Ser Leu Leu His Leu
    430                 435                 440 gcg gtg gag gcc ggg caa gag gag tgc gcc aag tgg ctg ctc ctc aac        1396
Ala Val Glu Ala Gly Gln Glu Glu Cys Ala Lys Trp Leu Leu Leu Asn
445                 450                 455                 460 aat gcc aac ccc aac ctg agc aac cgt agg ggc tcc acc ccg ttg cac        1444
Asn Ala Asn Pro Asn Leu Ser Asn Arg Arg Gly Ser Thr Pro Leu His
                465                 470                 475 atg gcc gtg gag agg agg gtg cgg ggt gtc gtg gag ctc ctg ctg gca        1492
Met Ala Val Glu Arg Arg Val Arg Gly Val Val Glu Leu Leu Leu Ala
            480                 485                 490 cgg aag atc agt gtc aac gcc aag gat gag gac cag tgg aca gcc ctc        1540
Arg Lys Ile Ser Val Asn Ala Lys Asp Glu Asp Gln Trp Thr Ala Leu
        495                 500                 505 cac ttt gca gcc cag aac ggg gat gag tct agc aca cgg ctg ctg ttg        1588
His Phe Ala Ala Gln Asn Gly Asp Glu Ser Ser Thr Arg Leu Leu Leu
    510                 515                 520 gag aag aac gcc tcg gtc aac gag gtg gac ttt gag ggc cgg acg ccc        1636
Glu Lys Asn Ala Ser Val Asn Glu Val Asp Phe Glu Gly Arg Thr Pro
525                 530                 535                 540 atg cac gtg gcc tgc cag cac ggg cag gag aat atc gtg cgc atc ctg        1684
Met His Val Ala Cys Gln His Gly Gln Glu Asn Ile Val Arg Ile Leu
                545                 550                 555
```

```
ctg cgc cga ggc gtg gac gtg agc ctg cag ggc aag gat gcc tgg ctg         1732
Leu Arg Arg Gly Val Asp Val Ser Leu Gln Gly Lys Asp Ala Trp Leu
            560                 565                 570 cca ctg cac tac gct gcc tgg cag ggc cac ctg ccc atc gtc aag ctg         1780
Pro Leu His Tyr Ala Ala Trp Gln Gly His Leu Pro Ile Val Lys Leu
        575                 580                 585 ctg gcc aag cag ccg ggg gtg agt gtg aac gcc cag acg ctg gat ggg         1828
Leu Ala Lys Gln Pro Gly Val Ser Val Asn Ala Gln Thr Leu Asp Gly
    590                 595                 600 agg acg cca ttg cac ctg gcc gca cag cgc ggc cac tac cgc gtg gcc         1876
Arg Thr Pro Leu His Leu Ala Ala Gln Arg Gly His Tyr Arg Val Ala
605                 610                 615                 620 cgc atc ctc atc gac ctg tgc tcc gac gtc aac gtc tgc agc ctg ctg         1924
Arg Ile Leu Ile Asp Leu Cys Ser Asp Val Asn Val Cys Ser Leu Leu
            625                 630                 635 gca cag aca ccc ctg cac gtg gcc gcg gag acg ggg cac acg agc act         1972
Ala Gln Thr Pro Leu His Val Ala Ala Glu Thr Gly His Thr Ser Thr
        640                 645                 650 gcc agg ctg ctc ctg cat cgg ggc gct ggc aag gag gcc gtg acc tca         2020
Ala Arg Leu Leu Leu His Arg Gly Ala Gly Lys Glu Ala Val Thr Ser
    655                 660                 665 gac ggc tac acc gct ctg cac ctg gct gcc cgc aac gga cac ctg gcc         2068
Asp Gly Tyr Thr Ala Leu His Leu Ala Ala Arg Asn Gly His Leu Ala
670                 675                 680 act gtc aag ctg ctt gtc gag gag aag gcc gat gtg ctg gcc cgg gga         2116
Thr Val Lys Leu Leu Val Glu Glu Lys Ala Asp Val Leu Ala Arg Gly
685                 690                 695                 700 ccc ctg aac cag acg gcg ctg cac ctg gct gcc gcc cac ggg cac tcg         2164
Pro Leu Asn Gln Thr Ala Leu His Leu Ala Ala Ala His Gly His Ser
            705                 710                 715 gag gtg gtg gag gag ttg gtc agc gcc gat gtc att gac ctg ttc gac         2212
Glu Val Val Glu Glu Leu Val Ser Ala Asp Val Ile Asp Leu Phe Asp
        720                 725                 730 gag cag ggg ctc agc gcg ctg cac ctg gcc gcc cag ggc cgg cac gca         2260
Glu Gln Gly Leu Ser Ala Leu His Leu Ala Ala Gln Gly Arg His Ala
    735                 740                 745 cag acg gtg gag act ctg ctc agg cat ggg gcc cac atc aac ctg cag         2308
Gln Thr Val Glu Thr Leu Leu Arg His Gly Ala His Ile Asn Leu Gln
750                 755                 760 agc ctc aag ttc cag ggc ggc cat ggc ccc gcc gcc aca ctc ctg cgg         2356
Ser Leu Lys Phe Gln Gly Gly His Gly Pro Ala Ala Thr Leu Leu Arg
765                 770                 775                 780 cga agc aag acc tag ctggctgcct gcggagaccg ggggtccacg tggggctctt         2411
Arg Ser Lys Thr * gtcctgtcct gtgttcctcg tggggatgga acgatcctgc gtggggcccc gttgtggctt        2471
acctaaatgt taaccaagca gaggtgacat ggtgccatca ggaggcggct gctgctgacc        2531
ggagtgtccc ctccaggtga agctggctca ggtgcacatg cccgctccat catcgatcta        2591
ggcacctgct gtctgaaggg accgtgggtc agaatcattt cgttgtgctc ctaatgggtc        2651
gctgaggctg gtctctcagt gatgaagccc caggcgtgga agcatccact ctctcctgag        2711
gcgagccacc ttgggttgct ggagctcacc agtcttgagg gaggtgcagg ggaaactgtg        2771 tttttatct tcatacatga cggtgggcag agaggcctgt cttaaagttt ccatggaatt         2831
gttttataaa atatcttaag agatgaatac cttatcagct gttgcttgaa acctgttaaa        2891
aatgttcata acattggata gtctagtctc taaatgatgg ctaagtagtg gggttggctt        2951
tgaaaacaat gttttatgca acaaggaacg aatggtagca gccagctttg cggggcgtat        3011
```

-continued

```
gtgtggccag ctcttaacca ttccagtcta ttacttgggt gagtccttgt ggacaaccac    3071
acacacgtgc ccacatggta ctagctgccg ttcgtttctc gttgcctaag atgttttggc    3131
aactctagag ccacaggcct aagagtcatt aaaaaattct cccttttgtaa cctcagtgct   3191 ggggactgag gcgagccccc tcaggtcgct ggagtgcacc agtcttgggg aagaggtgca    3251
ggagaagctg tgttttttat ctccacacgc agtatgaaga taaaattaca tagtattacc    3311
tagacataga cagtattacc taggtagatg cactgctcac ctgcacccct cccagctctc    3371
atttttgtta ggtgatttgg datagggata gtgttttggg gtatgggggg agtgtttctg    3431
acctgctttg cagacgtgcc tccgcacctc agcagtttgg ggtgtggccc cagggcggtt    3491
cttggatgta aaagatgtgg ccatctagcc tcgtaacttc actgtcacct gtgtcccata    3551
gggtgccttc tgaatactgt tattagaata gtttgttgc agaacgtgac cctgcgtgca     3611
aacatgtacc gtggcctggt atatgataga gattgatatt aatgtaccat gtatgttaat    3671
gtgaatctgt gggcaggata cttttccatg gcaggaaata tccaagctgt tgaaactggc    3731
tatgttttaa tatgcctcat tgtgccttta ctgttgtgtg gactgcgtga gggacaagaa    3791
gttccatttg atgtcaataa agcaaagtac ttgcctactt ttttgaanct gaaaaaaaaa    3851
aaaaaaagg                                                           3860
```

<210> SEQ ID NO 2
<211> LENGTH: 784
<212> TYPE: PRT
<213> ORGANISM: H. sapiens

<400> SEQUENCE: 2

```
Met Glu Gly Asp Gly Gly Thr Pro Trp Ala Leu Ala Leu Leu Arg Thr
 1               5                  10                  15

Phe Asp Ala Gly Glu Phe Thr Gly Trp Glu Lys Val Gly Ser Gly Gly
            20                  25                  30

Phe Gly Gln Val Tyr Lys Val Arg His Val His Trp Lys Thr Trp Leu
        35                  40                  45

Ala Ile Lys Cys Ser Pro Ser Leu His Val Asp Asp Arg Glu Arg Met
    50                  55                  60

Glu Leu Leu Glu Glu Ala Lys Lys Met Glu Met Ala Lys Phe Arg Tyr
65                  70                  75                  80

Ile Leu Pro Val Tyr Gly Ile Cys Arg Glu Pro Val Gly Leu Val Met
                85                  90                  95

Glu Tyr Met Glu Thr Gly Ser Leu Glu Lys Leu Leu Ala Ser Glu Pro
            100                 105                 110

Leu Pro Trp Asp Leu Arg Phe Arg Ile Ile His Glu Thr Ala Val Gly
        115                 120                 125

Met Asn Phe Leu His Cys Met Ala Pro Pro Leu Leu His Leu Asp Leu
    130                 135                 140

Lys Pro Ala Asn Ile Leu Leu Asp Ala His Tyr His Val Lys Ile Ser
145                 150                 155                 160

Asp Phe Gly Leu Ala Lys Cys Asn Gly Leu Ser His Ser His Asp Leu
                165                 170                 175

Ser Met Asp Gly Leu Phe Gly Thr Ile Ala Tyr Leu Pro Pro Glu Arg
            180                 185                 190

Ile Arg Glu Lys Ser Arg Leu Phe Asp Thr Lys His Asp Val Tyr Ser
        195                 200                 205

Phe Ala Ile Val Ile Trp Gly Val Leu Thr Gln Lys Lys Pro Phe Ala
```

```
        210                 215                 220
Asp Glu Lys Asn Ile Leu His Ile Met Val Lys Val Val Lys Gly His
225                 230                 235                 240
Arg Pro Glu Leu Pro Pro Val Cys Arg Ala Arg Pro Arg Ala Cys Ser
                    245                 250                 255
His Leu Ile Arg Leu Met Gln Arg Cys Trp Gln Gly Asp Pro Arg Val
                260                 265                 270
Arg Pro Thr Phe Gln Glu Ile Thr Ser Glu Thr Glu Asp Leu Cys Glu
            275                 280                 285
Lys Pro Asp Asp Glu Val Lys Glu Thr Ala His Asp Leu Asp Val Lys
        290                 295                 300
Ser Pro Pro Glu Pro Arg Ser Glu Val Val Pro Ala Arg Leu Lys Arg
305                 310                 315                 320
Ala Ser Ala Pro Thr Phe Asp Asn Asp Tyr Ser Leu Ser Glu Leu Leu
                    325                 330                 335
Ser Gln Leu Asp Ser Gly Val Ser Gln Ala Val Glu Gly Pro Glu Glu
                340                 345                 350
Leu Ser Arg Ser Ser Glu Ser Lys Leu Pro Ser Ser Gly Ser Gly
            355                 360                 365
Lys Arg Leu Ser Gly Val Ser Ser Val Asp Ser Ala Phe Ser Ser Arg
        370                 375                 380
Gly Ser Leu Ser Leu Ser Phe Glu Arg Glu Pro Ser Thr Ser Asp Leu
385                 390                 395                 400
Gly Thr Thr Arg Arg Pro Glu Glu Ala Cys Gly Cys His Arg Val
                    405                 410                 415
Arg Asp Thr Ser Lys Leu Met Lys Ile Leu Gln Pro Gln Asp Val Asp
                420                 425                 430
Leu Ala Leu Asp Ser Gly Ala Ser Leu Leu His Leu Ala Val Glu Ala
            435                 440                 445
Gly Gln Glu Glu Cys Ala Lys Trp Leu Leu Leu Asn Asn Ala Asn Pro
        450                 455                 460
Asn Leu Ser Asn Arg Arg Gly Ser Thr Pro Leu His Met Ala Val Glu
465                 470                 475                 480
Arg Arg Val Arg Gly Val Val Glu Leu Leu Ala Arg Lys Ile Ser
                    485                 490                 495
Val Asn Ala Lys Asp Glu Asp Gln Trp Thr Ala Leu His Phe Ala Ala
                500                 505                 510
Gln Asn Gly Asp Glu Ser Ser Thr Arg Leu Leu Leu Glu Lys Asn Ala
            515                 520                 525
Ser Val Asn Glu Val Asp Phe Glu Gly Arg Thr Pro Met His Val Ala
        530                 535                 540
Cys Gln His Gly Gln Glu Asn Ile Val Arg Ile Leu Leu Arg Arg Gly
545                 550                 555                 560
Val Asp Val Ser Leu Gln Gly Lys Asp Ala Trp Leu Pro Leu His Tyr
                    565                 570                 575
Ala Ala Trp Gln Gly His Leu Pro Ile Val Lys Leu Leu Ala Lys Gln
                580                 585                 590
Pro Gly Val Ser Val Asn Ala Gln Thr Leu Asp Gly Arg Thr Pro Leu
            595                 600                 605
His Leu Ala Ala Gln Arg Gly His Tyr Arg Val Ala Arg Ile Leu Ile
        610                 615                 620
Asp Leu Cys Ser Asp Val Asn Val Cys Ser Leu Leu Ala Gln Thr Pro
625                 630                 635                 640
```

-continued

```
Leu His Val Ala Ala Glu Thr Gly His Thr Ser Thr Ala Arg Leu Leu
            645                 650                 655

Leu His Arg Gly Ala Gly Lys Glu Ala Val Thr Ser Asp Gly Tyr Thr
        660                 665                 670

Ala Leu His Leu Ala Ala Arg Asn Gly His Leu Ala Thr Val Lys Leu
            675                 680                 685

Leu Val Glu Glu Lys Ala Asp Val Leu Ala Arg Gly Pro Leu Asn Gln
        690                 695                 700

Thr Ala Leu His Leu Ala Ala His Gly His Ser Glu Val Val Glu
705                 710                 715                 720

Glu Leu Val Ser Ala Asp Val Ile Asp Leu Phe Asp Glu Gln Gly Leu
            725                 730                 735

Ser Ala Leu His Leu Ala Ala Gln Gly Arg His Ala Gln Thr Val Glu
            740                 745                 750

Thr Leu Leu Arg His Gly Ala His Ile Asn Leu Gln Ser Leu Lys Phe
            755                 760                 765

Gln Gly Gly His Gly Pro Ala Ala Thr Leu Leu Arg Arg Ser Lys Thr
        770                 775                 780
```

<210> SEQ ID NO 3
<211> LENGTH: 2355
<212> TYPE: DNA
<213> ORGANISM: H. sapiens

<400> SEQUENCE: 3

```
atggagggcg acggcgggac cccatgggcc ctggcgctgc tgcgcacctt cgacgcgggc      60
gagttcacgg gctgggagaa ggtgggctcg ggcggcttcg ggcaggtgta caaggtgcgc     120
catgtccact ggaagacctg gctggccatc aagtgctcgc ccagcctgca cgtcgacgac     180
agggagcgca tggagctttt ggaagaagcc aagaagatgg agatggccaa gtttcgctac     240
atcctgcctg tgtatggcat ctgccgcgaa cctgtcggcc tggtcatgga gtacatggag     300
acgggctccc tggaaaagct gctggcttcg agccattgc catgggatct ccggttccga     360
atcatccacg agacggcggt gggcatgaac ttcctgcact gcatggcccc gccactcctg     420
cacctggacc tcaagcccgc gaacatcctg ctggatgccc actaccacgt caagatttct     480
gattttggtc tggccaagtg caacgggctg tcccactcgc atgacctcag catggatggc     540
ctgtttggca caatcgccta cctccctcca gagcgcatca gggagaagag ccggctcttc     600
gacaccaagc acgatgtata cagctttgcg atcgtcatct ggggcgtgct cacacagaag     660
aagccgtttg cagatgagaa gaacatcctg cacatcatgg tgaaggtggt gaagggccac     720
cgccccgagc tgccgcccgt gtgcagagcc cggccgcgcg cctgcagcca cctgatacgc     780
ctcatgcagc ggtgctggca gggggatccg cgagttaggc ccaccttcca agaaattact     840
tctgaaaccg aggacctgtg tgaaaagcct gatgacgaag tgaaagaaac tgctcatgat     900
ctggacgtga aaagcccccc ggagcccagg agcgaggtgg tgcctgcgag gctcaagcgg     960
gcctctgccc ccaccttcga taacgactac agcctctccg agcttctctc acagctggac    1020
tctggagttt cccaggctgt cgagggcccc gaggagctca gccgcagctc ctctgagtcc    1080
aagctgccat cgtccggcag tgggaagagg ctctcggggg tgtcctcggt ggactccgcc    1140
ttctcttcca gaggatcact gtcgctgtcc tttgagcggg aaccttcaac cagcgatctg    1200
ggtaccacaa gacgtccaga agaagaagct tgtggatgcc atcgtgtccg gacaccagc     1260
aaactgatga agatcctgca gccgcaggac gtggacctgg cactggacag cggtgccagc    1320
```

-continued

```
ctgctgcacc tggcggtgga ggccgggcaa gaggagtgcg ccaagtggct gctgctcaac    1380
aatgccaacc ccaacctgag caaccgtagg ggctccaccc cgttgcacat ggccgtggag    1440
aggagggtgc ggggtgtcgt ggagctcctg ctggcacgga agatcagtgt caacgccaag    1500
gatgaggacc agtggacagc cctccacttt gcagcccaga acggggatga gtctagcaca    1560
cggctgctgt tggagaagaa cgcctcggtc aacgaggtgg actttgaggg ccggacgccc    1620
atgcacgtgg cctgccagca cgggcaggag aatatcgtgc gcatcctgct cgccgaggc    1680 gtggacgtga gcctgcaggg caaggatgcc tggctgccac tgcactacgc tgcctggcag    1740
ggccacctgc ccatcgtcaa gctgctggcc aagcagccgg gggtgagtgt gaacgcccag    1800
acgctggatg ggaggacgcc attgcacctg gccgcacagc gcgggcacta ccgcgtggcc    1860
cgcatcctca tcgacctgtg ctccgacgtc aacgtctgca gcctgctggc acagacaccc    1920
ctgcacgtgg ccgcggagac ggggcacacg agcactgcca ggctgctcct gcatcggggc    1980
gctggcaagg aggccgtgac ctcagacggc tacaccgctc tgcacctggc tgcccgcaac    2040
ggacacctgg ccactgtcaa gctgcttgtc gaggagaagg ccgatgtgct ggcccgggga    2100
cccctgaacc agacggcgct gcacctggct gccgcccacg ggcactcgga ggtggtggag    2160
gagttggtca gcgccgatgt cattgacctg ttcgacgagc aggggctcag cgcgctgcac    2220
ctggccgccc agggccggca cgcacagacg gtggagactc tgctcaggca tggggcccac    2280
atcaacctgc agagcctcaa gttccagggc ggccatggcc ccgccgccac actcctgcgg    2340
cgaagcaaga cctag                                                    2355
```

<210> SEQ ID NO 4
<211> LENGTH: 272
<212> TYPE: PRT
<213> ORGANISM: Artificial Sequence
<220> FEATURE:
<223> OTHER INFORMATION: This is a consensus protein kinase domain. It
       occurs in 14171 according to a PFAM or a BLAST
       search.
<223> OTHER INFORMATION: Consensus Protein Kinase Domain

<400> SEQUENCE: 4

```
Tyr Glu Leu Leu Glu Lys Leu Gly Glu Gly Ser Phe Gly Lys Val Tyr
 1               5                  10                  15

Lys Ala Lys His Lys Thr Gly Lys Ile Val Ala Val Lys Ile Leu Lys
             20                  25                  30

Lys Glu Ser Leu Ser Leu Arg Glu Ile Gln Ile Leu Lys Arg Leu Ser
         35                  40                  45

His Pro Asn Ile Val Arg Leu Leu Gly Val Phe Glu Asp Thr Asp Asp
     50                  55                  60

His Leu Tyr Leu Val Met Glu Tyr Met Glu Gly Gly Asp Leu Phe Asp
 65                  70                  75                  80

Tyr Leu Arg Arg Asn Gly Pro Leu Ser Glu Lys Glu Ala Lys Lys Ile
                 85                  90                  95

Ala Leu Gln Ile Leu Arg Gly Leu Glu Tyr Leu His Ser Asn Gly Ile
            100                 105                 110

Val His Arg Asp Leu Lys Pro Glu Asn Ile Leu Leu Asp Glu Asn Gly
        115                 120                 125

Thr Val Lys Ile Ala Asp Phe Gly Leu Ala Arg Leu Leu Glu Lys Leu
    130                 135                 140

Thr Thr Phe Val Gly Thr Pro Trp Tyr Met Met Ala Pro Glu Val Ile
145                 150                 155                 160
```

-continued

```
Leu Glu Gly Arg Gly Tyr Ser Ser Lys Val Asp Val Trp Ser Leu Gly
            165                 170                 175

Val Ile Leu Tyr Glu Leu Leu Thr Gly Gly Pro Leu Phe Pro Gly Ala
            180                 185                 190

Asp Leu Pro Ala Phe Thr Gly Gly Asp Glu Val Asp Gln Leu Ile Ile
        195                 200                 205

Phe Val Leu Lys Leu Pro Phe Ser Asp Glu Leu Pro Lys Thr Arg Ile
    210                 215                 220

Asp Pro Leu Glu Glu Leu Phe Arg Ile Lys Lys Arg Arg Leu Pro Leu
225                 230                 235                 240

Pro Ser Asn Cys Ser Glu Glu Leu Lys Asp Leu Leu Lys Lys Cys Leu
            245                 250                 255

Asn Lys Asp Pro Ser Lys Arg Pro Gly Ser Ala Thr Ala Lys Glu Ile
            260                 265                 270
```

14171 PROTEIN KINASE, A NOVEL HUMAN PROTEIN KINASE AND USES THEREOF

CROSS-REFERENCE TO RELATED APPLICATION

This application claims the benefit of U.S. Provisional Application No. 60/182,096, filed Feb. 11, 2000, which is hereby incorporated in its entirety by reference.

FIELD OF THE INVENTION

The invention relates to a novel protein kinase nucleic acid sequence and protein. Also provided are vectors, host cells, and recombinant methods for making and using the novel molecules.

BACKGROUND OF THE INVENTION

Protein Kinases

Phosphate tightly associated with a molecule, e.g., a protein, has been known since the late nineteenth century. Since then, a variety of covalent linkages of phosphate to proteins have been found. The most common involve esterification of phosphate to serine, threonine, and tyrosine with smaller amounts being linked to lysine, arginine, histidine, aspartic acid, glutamic acid, and cysteine. The occurrence of phosphorylated molecules, e.g., proteins, implies the existence of one or more kinases, e.g., protein kinases, capable of phosphorylating various molecules, e.g., amino acid residues on proteins, and also of phosphatases, e.g., protein phosphatases, capable of hydrolyzing various phosphorylated molecules, e.g., phosphorylated amino acid residues on proteins.

Protein kinases play critical roles in the regulation of biochemical and morphological changes associated with cellular growth and division (D'Urso et al. (1990) *Science* 250:786–791; Birchmeier et al. (1993) *Bioessays* 15:185–189). They serve as growth factor receptors and signal transducers and have been implicated in cellular transformation and malignancy (Hunter et al. (1992) *Cell* 70:375–387; Posada et al. (1992) *Mol. Biol. Cell* 3:583–592; Hunter et al. (1994) *Cell* 79:573–582). For example, protein kinases have been shown to participate in the transmission of signals from growth-factor receptors (Sturgill et al. (1988) *Nature* 344:715–718; Gomez et al. (1991) *Nature* 353:170–173), control of entry of cells into mitosis (Nurse (1990) *Nature* 344:503–508; Maller (1991) *Curr. Opin. Cell Biol.* 3:269–275) and regulation of actin bundling (Husain-Chishti et al. (1988) *Nature* 334:718–721).

Protein kinases can be divided into different groups based on either amino acid sequence similarity or specificity for either serine/threonine or tyrosine residues. A small number of dual-specificity kinases have also been described. Within the broad classification, kinases can be further subdivided into families whose members share a higher degree of catalytic domain amino acid sequence identity and also have similar biochemical properties. Most protein kinase family members also share structural features outside the kinase domain that reflect their particular cellular roles. These include regulatory domains that control kinase activity or interaction with other proteins (Hanks et al. (1988) *Science* 241:42–52).

Extracellular-signal-regulated kinases/microtubule-associated protein kinases (Erk\MAPKs) and cyclin-directed kinases (Cdks) represent two large families of serine-threonine kinases (see Songyang et al., (1996) *Mol. Cell. Biol.* 16: 6486–6493). Both types of kinases function in cell growth, cell division, and cell differentiation, in response to extracellular stimulae. The Erk\MAPK family members are critical participants in intracellular signaling pathways. Upstream activators as well as the Erk\MAPK components are phosphorylated following contact of cells with growth factors or hormones or after cellular stressors, for example, heat, ultraviolet light, and inflammatory cytokines. These kinases transport messages that have been relayed from the plasma membrane to the cytoplasm by upstream kinases into the nucleus where they phosphorylate transcription factors and effect gene transcription modulation (Karin et al., (1995) *Curr. Biol.* 5: 747–757). Substrates of the Erk\MAPK family include c-fos, c-jun, APF2, and ETS family members Elk1, Sap1a, and c-Ets-1 (cited in Brott et al., (1998) *Proc. Natl Acad. Sci. USA* 95, 963–968).

Cdks regulate transitions between successive stages of the cell cycle. The activity of these molecules is controlled by phosphorylation events and by association with cyclin. Cdk activity is negatively regulated by the association of small inhibitory molecules (Dynlacht, (1997) *Nature* 389:148–152). Cdk targets include various transcriptional activators such as p110Rb, p107 and transcription factors, such as p53, E2F and RNA polymerase II, as well as various cytoskeletal proteins and cytoplasmic signaling proteins (cited in Brott et al., above).

A protein has been isolated in Drosophilia, designated nemo, which has homology to Erk\MAPKs and Cdks. A mammalian homologue of nemo, designated NLK, has been reported (Brott et al., above). This protein kinase autophosphorylates and localizes to a great extent in the nucleus. This protein showed homology to both families of kinases (Erk\MAPKs and Cdks). It did not possess the characteristic MAPK phosphorylation motif TXY in the conserved kinase domain VIII. It instead exhibited the sequence TQE resembling the THE sequence found in some Cdks.

More recently, it was shown that NLK could down-regulate HMG-domain-containing proteins related to POP-1. The signaling protein Wnt regulates transcription factors containing high-mobility group (HMG) domains to direct decisions on cell fate during animal development. In *C. elegans*, the HMG-domain-containing repressor POP-1 distinguishes the fate of anterior daughter cells from posterior daughter cells throughout development. Wnt signaling down-regulates POP-1 activity in posterior daughter cells, for example, E. Meneghini et al., (1999) *Nature* 399: 793–797, show that the genes MOM-4 and LIT-1 were also required to down-regulate POP-1 not only in E but in other posterior daughter cells. MOM-4 and LIT-1 are homologous to the mammalian components of the mitogen-activated protein kinase (MAPK) pathway of TAK-1 (transforming growth factor beta activated kinase (and NLK) nemo-like kinase, respectively. MOM-4 and TAK-1 bind related proteins that promote their kinase activity. The authors of the report concluded that a MAPK-related pathway cooperates with Wnt signal transduction to down-regulate POP-1 activity.

In a further report by the same group (Ishitani et al, (1999) *Nature* 399: 798–802), it was shown that the TAK-1-NLK-MAPK-related pathway antagonizes signaling between beta-catenin and transcription factor TCF. The Wnt-signaling pathway regulates developmental processes through a complex of beta-catenin and the T-cell factor/lymphoid enhancer factor (TCF\LEF) family of high-mobility group transcription factors. Wnt stabilizes beta-catenin which then binds to TCF and activates gene transcription. This signal pathway is conserved in vertebrates, Drosophilia and *C. elegans*. In *C. elegans*, MOM-4 and LIT-1 regulate Wnt signaling during embryogenesis. MOM-4 is homologous to TAK-1 (a kinase activated by transforming growth factor beta). LIT-1 is homologous to mitogen-activated protein kinase kinase kinase (MAP3K) and MAP kinase (MAPK)-related NEMO-like kinase (NLK) in mammalian cells. This raised the possibility that TAK-1 and NLK were involved in Wnt signaling in mammalian cells. The authors reported that TAK-1 activation stimulates NLK activity and down-regulates transcriptional activation mediated by beta-catenin and TCF. Injection of NLK suppressed the induction of axis duplication by microinjected beta-catenin in Xenopus embryos. NLK was shown to phosphorylate TCF\LEF factors and inhibit the interaction of the beta-catenin-TCF complex with DNA. Accordingly, the TAK-1-NLK-MAPK-like pathway was shown to negatively regulate the Wnt signaling pathway.

Members of the tumor necrosis factor receptor superfamily have an important role in the induction of cellular signals resulting in cell growth, differentiation, and death. See Smith et al. (1994) *Cell* 76:959–962. Tumor necrosis factor receptor-1 recruits and assembles a signaling complex containing a number of death domain-containing proteins and a serine/threonine kinase, RIP, that mediates tumor necrosis factor-induced activation of nuclear factor-κB. See Stanger et al. (1995) *Cell* 81:513–523 and Kelliher et al. (1998) *Immunity* 8:297–303. Recently, another RIP-like kinase has been characterized, designated "CARDIAK," which contains a serine/threonine kinase domain as well as a carboxy-terminal caspase recruiting domain (CARD) (Thome, et al. (1998) *Current Biology* 8:885–888). Overexpression of this serine/threonine kinase induced the activation of both nuclear factor-κB and Jun N-terminal kinase. This kinase also interacted with the tumor necrosis factor receptor-associated factors TRAF-1 and TRAF-2. A dominant negative form of TRAF-2 inhibited CARDIAK-induced nuclear factor-κB activation. The data in the report suggested that CARDIAK is involved in nuclear factor-κB/Jun N-terminal kinase signaling.

Protein kinases play critical roles in cellular growth. Therefore, novel protein kinase polynucleotides and proteins are useful for modulating cellular growth, differentiation and/or development.

Programmed Cell Death

In multicellular organisms, homeostasis is maintained by balancing the rate of cell proliferation against the rate of cell death. Cell proliferation is influenced by numerous growth factors and the expression of proto-oncogenes, which typically encourage progression through the cell cycle. In contrast, numerous events, including the expression of tumor suppressor genes, can lead to an arrest of cellular proliferation.

In differentiated cells, a particular type of cell death called apoptosis occurs when an internal suicide program is activated. This program can be initiated by a variety of external signals as well as signals that are generated within the cell in response to, for example, genetic damage. Dying cells are eliminated by phagocytes, without an inflammatory response.

Programmed cell death is a highly regulated process (Wilson (1998) *Biochem. Cell. Biol.* 76:573–582). The death signal is then transduced through various signaling pathways that converge on caspase-mediated degradative cascades resulting in the activation of late effectors of morphological and physiological aspects of apoptosis, including DNA fragmentation and cytoplasmic condensation. In addition, regulation of programmed cell death may be integrated with regulation of energy, redox- and ion homeostasis in the mitochondria (reviewed by (Kroemer, 1998)), and/or cell-cycle control in the nucleus and cytoplasm (reviewed by (Choisy-Rossi and Yonish-Rouach, 1998; Dang, 1999; Kasten and Giordano, 1998)). Many mammalian genes regulating apoptosis have been identified as homologs of genes originally identified genetically in *Caenorhabditis elegans* or *Drosophila melanogaster*, or as human oncogenes. Other programmed cell death genes have been found by domain homology to known motifs, such as death domains, that mediate protein-protein interactions within the programmed cell death pathway.

The mechanisms that mediate apoptosis include, but are not limited to, the activation of endogenous proteases, loss of mitochondrial function, and structural changes, such as disruption of the cytoskeleton, cell shrinkage, membrane blebbing, and nuclear condensation due to degradation of DNA. The various signals that trigger apoptosis may bring about these events by converging on a common cell death pathway that is regulated by the expression of genes that are highly conserved.

Caspases (cysteine proteases having specificity for aspartate at the substrate cleavage site) are central to the apoptotic program. These proteases are responsible for degradation of cellular proteins that lead to the morphological changes seen in cells undergoing apoptosis. One of the human caspases was previously known as the interleukin-1β (IL-1β) converting enzyme (ICE), a cysteine protease responsible for the processing of pro-IL-1β to the active cytokine. Overexpression of ICE in Rat-1 fibroblasts induces apoptosis (Miura et al. (1993) *Cell* 75:653).

Many caspases and proteins that interact with caspases possess domains of about 60 amino acids called a caspase recruitment domain (CARD). Apoptotic proteins may bind to each other via their CARDs. Different subtypes of CARDs may confer binding specificity, regulating the activity of various caspases. (Hofmann et al. (1997) *TIBS* 22:155).

The functional significance of CARDs have been demonstrated in two recent publications. Duan et al. (1997) *Nature* 385:86 showed that deleting the CARD at the N-terminus of RAIDD, a newly identified protein involved in apoptosis, abolished the ability of RAIDD to bind to caspases. In addition, Li et al. (1997) *Cell* 91:479 showed that the N-terminal 97 amino acids of apoptotic protease activating factor-1 (Apaf-1) was sufficient to confer caspase-9-binding ability.

Thus, programmed cell death (apoptosis) is a normal physiological activity necessary to proper and differentiation in all vertebrates. Defects in apoptosis programs result in disorders including, but not limited to, neurodegenerative disorders, cancer, immunodeficiency, heart disease and autoimmune diseases (Thompson et al. (1995) *Science* 267:1456).

In vertebrate species, neuronal programmed cell death mechanisms have been associated with a variety of developmental roles, including the removal of neuronal precursors which fail to establish appropriate synaptic connections (Oppenheim et al. (1991) *Annual Rev. Neuroscience* 14:453–501), the quantitative matching of pre- and post-synaptic population sizes (Herrup et al. (1987) *J. Neurosci.* 7:829–836), and sculpting of neuronal circuits, both during development and in the adult (Bottjer et al. (1992) *J. Neurobiol.* 23:1172–1191).

Inappropriate apoptosis has been suggested to be involved in neuronal loss in various neurodegenerative diseases such as Alzheimer's disease (Loo et al. (1993) *Proc. Natl. Acad. Sci.* 90:7951–7955), Huntington's disease (Portera-Cailliau et al. (1995) *J. Neurosc.* 15:3775–3787), amyotrophic lateral sclerosis (Rabizadeh et al. (1995) *Proc. Natl. Acad. Sci.* 92:3024–3028), and spinal muscular atrophy (Roy et al. (1995) *Cell* 80:167–178).

In addition, improper expression of genes involved in apoptosis has been implicated in carcinogenesis. Thus, it has been shown that several "oncogenes" are in fact involved in apoptosis, such as in the Bcl family.

Accordingly, genes involved in apoptosis are important targets for therapeutic intervention. It is important, therefore, to identify novel genes involved in apoptosis or to discover whether known genes function in this process.

SUMMARY OF THE INVENTION

An isolated nucleic acid molecule corresponding to a protein kinase nucleic acid sequence is provided. Additionally an amino acid sequence corresponding to the polynucleotide is encompassed. In particular, the present invention provides for an isolated nucleic acid molecule (SEQ ID NO:1) comprising the nucleotide sequence encoding the amino acid sequence shown in SEQ ID NO:2. Further provided is a protein kinase polypeptide having an amino acid sequence encoded by the nucleic acid molecule described herein. The coding sequence for human 14171 is shown in SEQ ID NO:3.

The present invention also provides vectors and host cells for recombinant expression of the nucleic acid molecule described herein, as well as methods of making such vectors and host cells and for using them for production of the polypeptide or peptides of the invention by recombinant techniques.

The protein kinase molecule of the present invention is useful for modulating cellular growth and/or cellular metabolic pathways particularly for regulating one or more proteins involved in growth and metabolism. Accordingly, in one aspect, this invention provides an isolated nucleic acid molecule encoding a protein kinase protein or biologically active portions thereof, as well as nucleic acid fragments suitable as primers or hybridization probes for the detection of protein kinase-encoding nucleic acids.

Another aspect of this invention features an isolated or recombinant kinase protein and polypeptide. Preferred protein kinase proteins and polypeptides possess at least one biological activity possessed by naturally-occurring protein kinase.

Variant nucleic acid molecules and polypeptides substantially homologous to the nucleotide and amino acid sequence set forth in the sequence listing are encompassed by the present invention. Additionally, fragments and substantially homologous fragments of the nucleotide and amino acid sequence are provided.

Antibodies and antibody fragments that selectively bind the protein kinase polypeptide and fragments are provided. Such antibodies are useful in detecting the protein kinase polypeptide as well as in modulating cellular growth and metabolism.

In another aspect, the present invention provides a method for detecting the presence of protein kinase activity or expression in a biological sample by contacting the biological sample with an agent capable of detecting an indicator of protein kinase activity such that the presence of protein kinase activity is detected in the biological sample.

In yet another aspect, the invention provides a method for modulating protein kinase activity comprising contacting a cell with an agent that modulates (inhibits or stimulates) protein kinase activity or expression such that protein kinase activity or expression in the cell is modulated. In one embodiment, the agent is an antibody that specifically binds to kinase protein. In another embodiment, the agent modulates expression of protein kinase protein by modulating transcription of a protein kinase gene, splicing of a protein kinase mRNA, or translation of a protein kinase mRNA. In yet another embodiment, the agent is a nucleic acid molecule having a nucleotide sequence that is antisense to the coding strand of the protein kinase mRNA or the protein kinase gene.

In one embodiment, the methods of the present invention are used to treat a subject having a disorder characterized by aberrant protein kinase protein activity or nucleic acid expression by administering an agent that is a protein kinase modulator to the subject. In one embodiment, the protein kinase modulator is a protein kinase protein. In another embodiment, the protein kinase modulator is a protein kinase nucleic acid molecule. In other embodiments, the protein kinase modulator is a peptide, peptidomimetic, or other small molecule.

The present invention also provides a diagnostic assay for identifying the presence or absence of a genetic lesion or mutation characterized by at least one of the following: (1) aberrant modification or mutation of a gene encoding a protein kinase protein; (2) misregulation of a gene encoding a protein kinase protein; and (3) aberrant post-translational modification of a protein kinase protein, wherein a wild-type form of the gene encodes a protein with a protein kinase activity.

In another aspect, the invention provides a method for identifying a compound that binds to or modulates the activity of a protein kinase protein. In general, such methods entail measuring a biological activity of a protein kinase protein in the presence and absence of a test compound and identifying those compounds that alter the activity of the protein kinase protein.

The invention also features methods for identifying a compound that modulates the expression of the protein kinase gene by measuring the expression of the protein kinase sequence in the presence and absence of the compound.

The invention also provides compounds identified by the screening methods described herein.

Other features and advantages of the invention will be apparent from the following detailed description and claims.

BRIEF DESCRIPTION OF THE DRAWINGS

Figure 1A-2:
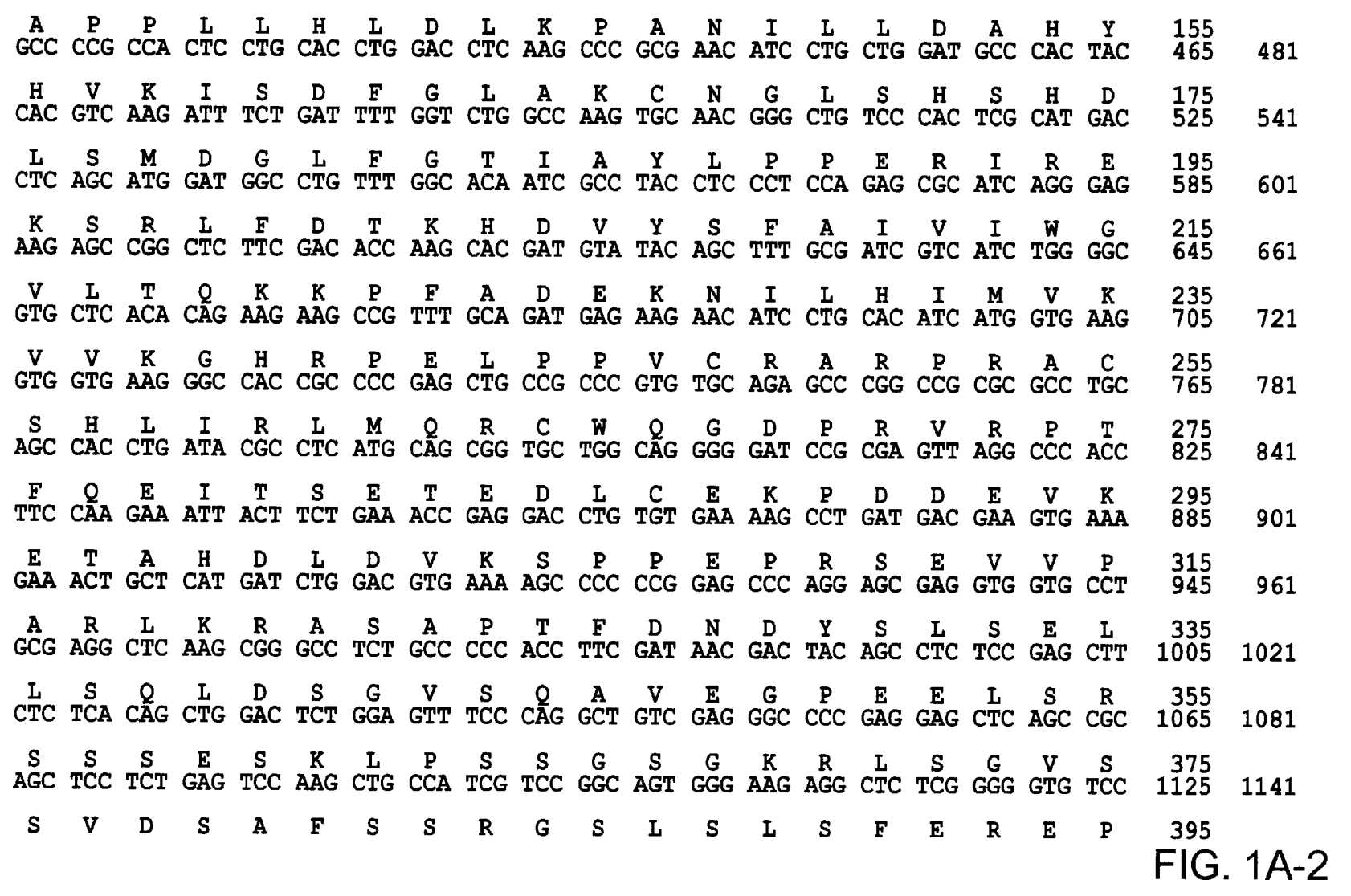

FIGS. 1A-1 to 1C show the 14171 nucleotide sequence (SEQ ID NO:1) and the deduced amino acid sequence (SEQ ID NO:2).

FIGS. 2A-1 to 2B show an analysis of the 14171 open reading frame for amino acids corresponding to specific functional sites. The figures show the position of three glycosylation sites, a glycosaminoglycan attachment site, four cAMP and cGMP dependent protein kinase phosphorylation sites, ten protein kinase C phosphorylation sites, twelve casein kinase II phosphorylation sites, nine N-myristoylation sites, an amidation site, a protein kinase ATP binding region signature, a serine/threonine protein kinase active site signature, and a eukaryotic and viral aspartyl protease active site. In the case of glycosylation, the actual modified residue is the first amino acid of the indicated site. In the case of cAMP and cGMP dependent protein kinase phosphorylation, the actual modified residue is the last amino acid in the indicated site. In the case of protein kinase C phosphorylation, the actual modified residue is the first amino acid in the indicated sites. In the case of casein kinase II phosphorylation, the actual modified residue is the first amino acid in the indicated sites. In the case of N-myristoylation, the actual modified residue is the first amino acid in the indicated site.

FIG. 5 depicts the expression of 14171 in the following human tissues: lung (column 1), brain (column 2), normal liver (columns 3–5), HepG2 (columns 6 and 8), HepG2.2.15 (columns 7 and 9), Hepatitis C positive liver (columns 10 and 11), and ganglia (columns 12–14).

FIG. 6 depicts the alignment of the protein kinase domain of human 14171 with a consensus amino acid sequence derived from a hidden Markov model. The lower sequence is the consensus amino acid sequence (SEQ ID NO:4), while the upper amino acid sequence corresponds to amino acids 22 to 279 of SEQ ID NO:2.

DETAILED DESCRIPTION OF THE INVENTION

Figure 3:
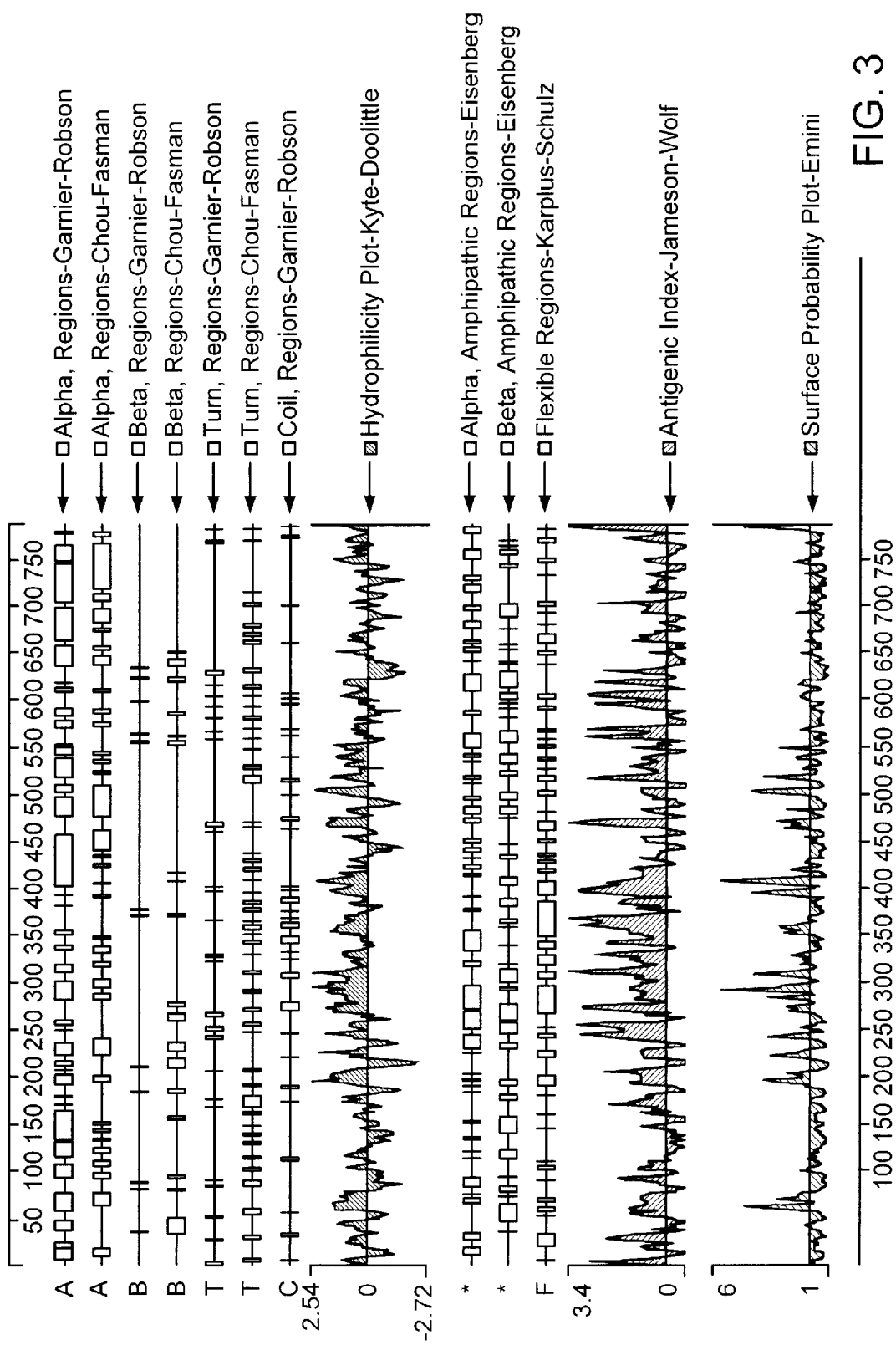
FIG. 3 shows an analysis of the 14171 amino acid sequence: αβ turn and coil regions; hydrophilicity; amphipathic regions; flexible regions; antigenic index; and surface probability.

The present invention is based, at least in part, on the identification of a novel molecule, the 14171 kinase, which is a protein kinase. When referring to the 14171 protein kinase, the term "kinase" is intended to mean a protein having protein kinase activity or to a nucleic acid encoding the protein. The kinase nucleic acid and polypeptide molecules of the invention play a role in, or function in, signaling pathways associated with cellular growth and/or cellular metabolic pathways, and, in the present case, is also involved in a productive viral infection. These growth and metabolic pathways are described in Lodish et al. (1995) *Molecular Cell Biology* (Scientific American Books Inc., New York, N.Y.) and Stryer *Biochemistry*, (W. H. Freeman, New York), the contents of which are incorporated herein by reference. In one embodiment, the kinase molecule modulates the activity of one or more proteins involved in viral infection, cellular growth, or differentiation, e.g., HBV-infected cells. In another embodiment, the kinase molecule of the present invention is capable of modulating the phosphorylation state of a kinase molecule or the phosphorylation state of one or more proteins involved in apoptosis, viral infection, cellular growth, or differentiation, e.g., HBV-infected cells. See also Lodish et al. and Stryer, supra. In addition, kinases of the present invention are targets of drugs described in Goodman and Gilman (1996), *The Pharmacological Basis of Therapeutics* ($9^{th}$ ed.) Hartman & Limbard Editors, the contents of which are incorporated herein by reference. Particularly, the kinase of the invention modulates phosphorylation in HBV virus-infected tissues and cells, such as liver.

The kinase of the invention contains domains or motifs, identified by routine homology searching procedures, for example Pfam and Prosite analysis. Such analysis has identified six ankyrin motifs and homology to various ankyrin proteins from humans and other species and to ankyrin-like proteins. Birkenmeier et al. ((1998) *Genomics* 50:79–88) has shown an erythroid ankyrin gene producing an isoform containing an amino terminal membrane anchor. Kordeli et al. ((1998) *J. Cell Sci.* 111:2197–2207) has shown that ankyrin G is associated with the post-synaptic membrane and sarcoplasmic reticulum in skeletal muscle fiber. Zhang et al. ((1998) *J. Biol. Chem.* 273:18681–18684) has shown the structure of the ankyrin binding domain of α-sodium potassium ATPase. Miraglia et al. ((1998) *J. Pediat.* 132:117–120) has shown a high frequency of spontaneous mutations in the ankyrin gene in children with heredity spherocytosis. Randon et al. ((1997) *Br. J. Haematol.* 96:500–506) has shown frequent spontaneous mutations of the ankyrin gene mimicking a recessive mode of transmission in heredity spherocytosis and described three new ankyrin variants. Accordingly, the kinase of the invention, containing an ankyrin motif, contains, in addition to kinase activity, functions of the ankyrin protein including, but not limited to, those discussed in the references above, incorporated herein by reference for these functions and for assays for detecting such functions. The ankyrin repeat domains may confer a membrane association on the polypeptides of the invention.

The kinase of the invention also contains a kinase motif for serine/threonine kinase activity. The serine/threonine kinase, RIP, (Stanger et al. (1995) *Cell* 81:513–523) mediates tumor necrosis factor-induced nuclear factor-κB activation, as discussed above. In fact, the protein kinase of the invention, having a kinase domain at the 5' end and the 6 ankyrin repeats at the 3' end shows similarity of the kinase to RIP. Recently the serine/threonine kinase CARDIAK has been shown to induce activation of both nuclear factor-κB and Jun N-terminal kinase. The gene was shown to induce apoptosis in 293T cells. It was shown to function via the nuclear factor κB signal pathway by means of a luciferase reporter with nuclear factor-κB binding sites in 293T cells. The gene was also shown to interact through binding to TRAF-1 and TRAF-2. Accordingly, the serine/threonine kinase of the invention, shown by BLAST homology searching to contain homology to a human RIP-like kinase, is likely to function in this signal pathway, including the phosphorylation and activation of these substrates as well as interactions with other molecules of the pathway, such as the TRAF family. Further, like CARDIAK, the kinase of the invention may contain autophosphorylation activity.

The gene encoding the protein kinase of the invention maps to human chromosome 21 with a syntenic chromosome, possibly mo10, 17, or 16. Flanking markers include WI-5330 (7.1cR) WI-3679 (4.7 cR). Nearby mutations/loci include DFNB8, deafness, neurosensory, autosomal recessive 8; DSCR Down's Syndrome critical region, included; KNO, knobloch syndrome. Nearby known genes include PAPPA, FRG1, WHITE1, TFF3, MX1, TFF2, PDE9A, CBS, PDXK, C21ORF2, ES1, PFKL, TRPC7, ADARB1, ITGB2, COL18A1, SLC19A1, LSS, HRTM1L1.

As used herein, a protein kinase includes a protein or polypeptide that is capable of modulating its own phosphorylation state or the phosphorylation state of a different protein or polypeptide. Such a change comprises alteration of any of the various bonds, oxidation, reduction of the molecule, to effect the addition of phosphate. Protein kinases can have a specificity for (i.e., a specificity to phosphorylate) serine/threonine residues, tyrosine residues, or both serine/threonine and tyrosine residues, e.g., the dual-specificity protein kinases. As referred to herein, protein kinases, preferably include a catalytic domain of about 200–400 amino acid residues in length, preferably about 200–300 amino acid residues in length, or more preferably about 250–300 amino acid residues in length, which includes preferably 5–20, more preferably 5–15, or most preferably 11 highly conserved motifs or subdomains separated by sequences of amino acids with reduced or minimal conservation. Specificity of a protein kinase for phosphorylation of either tyrosine or serine/threonine can be predicted by the sequence of two of the subdomains (VIb and VIII) in which different residues are conserved in each class (as described in, for example, Hanks et al. (1988) *Science* 241:42–52, the contents of which are incorporated herein by reference). These subdomains are also described in further detail herein.

Protein kinases play a role in signaling pathways associated with cellular growth. For example, protein kinases are involved in the regulation of signal transmission from cellular receptors, e.g., growth-factor receptors, entry of cells into mitosis, and the regulation of cytoskeleton function, e.g., actin bundling.

Assays for measuring protein kinase activity are well known in the art depending on the particular protein kinase. Specific assay protocols are available in standard sources known to the ordinarily skilled artisan. For example, see "Kinases" in Ausubel et al., eds. (1994–1998) *Current Protocols in Molecular Biology* (3) and references cited therein protein kinase-specific protocols available at the Protein Kinase Resource website maintained by the University of California at San Diego, San Diego, Calif. (pkr.sdsc.edu).

Further, apoptosis-specific assays may be used to identify modulators of any of the target nucleic acids or proteins of the present invention, which proteins and/or nucleic acids are related to apoptosis. Accordingly, an agent that modulates the level or activity of any of these nucleic acids or proteins can be identified by means of apoptosis-specific assays. For example, high throughput screens exist to identify apoptotic cells by the use of chromatin or cytoplasmic-specific dyes. Thus, hallmarks of apoptosis, cytoplasmic condensation and chromosome fragmentation, can be used as a marker to identify modulators of any of the gene related to programmed-cell death described herein. Other assays include, but are not limited to, the activation of specific endogenous proteases, loss of mitochondrial function, cytoskeletal disruption, cell shrinkage, membrane blebbing, and nuclear condensation due to degradation of DNA.

Apoptosis can be actively induced in animal cells by a diverse array of triggers that range from ionizing radiation to hypothermia to viral infections to immune reactions. Majno et al. (1995) *Amer. J. Pathol.* 146:3–15; Hockenberry et al. (1995) *Bio Essays* 17:631–638; Thompson et al. (1995) *Science* 267:1456–1462.

Apoptosis can be triggered by the addition of apoptosis-promoting ligands to a cell in culture or in vivo. Apoptosis can also be triggered by decreasing or removing an apoptosis-inhibiting or survival-promoting ligand. Accordingly, apoptosis is triggered in view of the fact that the cell lacks a signal from a cell surface survival factor receptor. Ligands include, but are not limited to, FasL. Death-inhibiting ligands include, but are not limited to, IL-2. See Hetts et al. (1998) *JAMA* 279:300–307 (incorporated by reference in its entirety for teaching of ligands involved in active and passive apoptosis pathways). Central in the pathway, and also serving as potential molecules for inducing (or releasing from inhibition) apoptosis pathways include FADD, caspases, human CED4 homolog (also called apoptotic protease activating factor 1), the Bcl-2 family of genes including, but not limited to, apoptosis promoting (for example, Bax and Bad) and apoptosis inhibiting (for example, Bcl-2 and Bcl-$x_l$) molecules. See Hetts et al., above.

Multiple caspases upstream of caspase-3 can be inhibited by viral proteins such as cowpox, CrmA, and baculovirus, p35. Synthetic tripeptides and tetrapeptides inhibit casepase-3 specifically (Hetts, above).

Accordingly, cellular and animal models also exist for studying expression or function of the kinase protein sequences in apoptosis and with regard to their effect on apoptosis. Such model systems can be applied in the context of the assays described herein below, for example the effect of specific mutations in the kinase protein, the effect of compounds on the kinase protein, and any of the other assays in which the effect of altered expression or activity of the kinase protein is within the context of effects on apoptosis.

Inhibition or over-stimulation of the activity of kinases involved in signaling pathways associated with cellular growth can lead to perturbed cellular growth, which can in turn lead to cellular growth related-disorders. As used herein, a "cellular growth-related disorder" includes a disorder, disease, or condition characterized by a deregulation, e.g., an upregulation or a downregulation, of cellular growth. Cellular growth deregulation may be due to a deregulation of cellular proliferation, cell cycle progression, cellular differentiation and/or cellular hypertrophy. Examples of cellular growth related disorders include cardiovascular disorders such as heart failure, hypertension, atrial fibrillation, dilated cardiomyopathy, idiopathic cardiomyopathy, or angina; proliferative disorders or differentiative disorders such as cancer, e.g., liver cancer, melanoma, prostate cancer, cervical cancer, breast cancer, colon cancer, or sarcoma. Disorders associated with virally-infected cells or tissues are also encompassed. The compositions are useful for the treatment of viral infection, such as DNA virus infection, including but not limited to HBV.

RNA was isolated from HepG2 (immortalized human hepatocyte cells) and a HepG2 cell line stably transfected with the HBV genome. These cell lines can be used to screen for anti-HBV compounds. The RNA was labeled by synthesizing $P^{33}$-labeled cDNA and hybridized to a gene array containing novel human genes identified by the inventors. 14171 RNA was found to be 3.6-fold more abundant in HBV-infected HepG2 cells than in uninfected HepG2 cells.

The disclosed invention accordingly relates to methods and compositions for the modulation, diagnosis, and treatment of disorders associated with, caused by, or related to viral infection. These disorders can manifest as immune, inflammatory, respiratory, hematological, cardiovascular, and other disorders including, but not-limited to, AIDS, virus associated leukemias, lymphomas, sarcomas, and carcinomas, herpetic infections and collateral symptoms, EBV infection, including mononucleosis, hepatitis virus infection, including A, B, C, and D viruses, with virally induced liver cancer and viral pneumonias.

Viruses include, but are not limited to, those identified with carcinogenesis, including hepatitis B virus (HBV) and liver cancer, Epstein-Barr virus (EBV), and lymphoma, human T-cell lymphotrophic virus Type I (HTLV-1) and leukemia, and human Herpes virus 8 (HHV-8) and Kaposi sarcoma. Virus families to which the invention pertains include but are not limited to Adenoviridae, Picornaviridae, Coronaviridae, Orthomyxoviridae, Paramyxoviridae, Reoviridae, Caliciviridae, Hepadnaviridae, Viroid-like, Flaviviridae, Norwalk-like, Togaviridae, Parvoviridae, Poxviridae, Herpesviridae, Retroviridae, Reoviridae (Orbivirus), Arenaviridae, Bunyaviridae, Filoviridae?, Hantavirus, and Papovaviridae. Respiratory diseases have been associated with Adenovirus, Echovirus, Rhinovirus, Coxsackievirus, Coronavirus, Influenza viruses A, B, Parainfluenza virus 1–4, and Respiratory syncytial virus. Viral diseases of the respiratory system include, but are not limited to, lower respiratory tract infections, conjunctivitis, diarrhea; upper respiratory tract infections, pharyngitis, rash; pleurodynia, herpangina, hand-foot-and-mouth disease; influenza, croup, bronchiolitis, and pneumonia. Digestive diseases have been associated with Mumps virus, Rotavirus, Norwalk agent, Hepatitis A Virus, Hepatitis B Virus, Hepatitis D Virus, Hepatitis C Virus, and Hepatitis E Virus. These include but are not limited to mumps, pancreatitis, orchitis; childhood diarrhea; gastroenteritis; acute viral hepatitis; acute or chronic hepatitis; with HBV, acute or chronic hepatitis; and enterically transmitted hepatitis. Systemic viral pathogens associated with skin eruptions include, but are not limited to, Measles virus, Rubella virus, Parvovirus, Vaccinia virus, Varicella-zoster virus, Herpes simplex virus 1, and Herpes simplex virus 2. Disease expression includes, but is not limited to, Measles (rubeola); German measles (rubella); Erythema infectiosum, aplastic anemia; smallpox; chickenpox, shingles; "cold sore"; and genital herpes. Systemic viral pathogens associated with hematopoietic disorders include Cytomegalovirus, Epstein-Barr virus, HTLV-I, HTLV-II, HIV-1 and HIV-2. Disease expression includes, but is not limited to, Cytomegalic inclusion disease; infectious mononucleosis; adult T-cell leukemia; tropical spastic paraparesis; and AIDS. Viral pathogens associated with Arboviral and Hemorrhagic fevers include, but are not limited, Dengue virus 1–4, yellow fever virus, Colorado tick fever virus, and regional hemorrhagic fever viruses. Disease expression includes, but is not limited to, Dengue, hemorrhagic fever; yellow fever; Colorado tick fever; Bolivian, Argentinian, Lassa fever; Crimean-Congo, Hantaan, sandfly fever; Ebola, Marburg disease; Korean, U.S. pneumonia. Viral pathogens associated with warty growths include Papillomavirus and molluscum virus. Disease expression includes, but is not limited to, Condyloma; cervical carcinoma; and molluscum contagiosum. Viral pathogens associated with diseases of the central nervous system include, but are not limited to, Poliovirus, Rabiesvirus, JC virus, and Arboviral encephalitis viruses. Disease expression includes, but is not limited to, Poliomyelitis; Rabies; progressive multifocal leukoencephalopathy (opportunistic); Eastern, Western, Venezuelan, St. Louis, California group.

Other especially relevant disorders include those that are associated with programmed cell death. These include, but are not limited to, those described herein and also in the references above, that are incorporated herein by reference for disclosure of disorders associated with programmed cell death.

As used herein, "programmed cell death" refers to a genetically regulated process involved in the normal development of multicellular organisms. This process occurs in cells destined for removal in a variety of normal situations, including larval development of the nematode *C. elegans*, insect metamorphosis, development in mammalian embryos, including the nephrogenic zone in the developing kidney, and regression or atrophy (e.g., in the prostate after castration). Programmed cell death can occur following the withdrawal of growth and trophic factors in many cells, nutritional deprivation, hormone treatment, ultraviolet irradiation, and exposure to toxic and infectious agents including reactive oxygen species and phosphatase inhibitors, e.g., okadaic acid, calcium ionophores, and a number of cancer chemotherapeutic agents. See Wilson (1998) *Biochem. Cell Biol.* 76:573–582 and Hetts (1998) *JAMA* 279:300–307, the contents of which are incorporated herein by reference. Thus, the protein of the invention can modulate a programmed cell death pathway activity and provide a novel diagnostic target and therapeutic agents for disorders characterized by deregulated programmed cell death, particularly in cells that express the protein.

As used herein, a "disorder characterized by deregulated programmed cell death" refers to a disorder, disease or condition which is characterized by a deregulation, e.g., an upregulation or a downregulation, of programmed cell death. Programmed cell death deregulation can lead to deregulation of cellular proliferation and/or cell cycle progression. Examples of disorders characterized by deregulated programmed cell death include, but are not limited to, neurodegenerative disorders, e.g., Alzheimer's disease, dementias related to Alzheimer's disease (such as Pick's disease), Parkinson's and other Lewy diffuse body diseases, multiple sclerosis, amyotrophic lateral sclerosis, progressive supranuclear palsy, epilepsy, Jakob-Creutzfieldt disease, or AIDS related dementias; myelodysplastic syndromes, e.g., aplastic anemia; ischemic injury, e.g., myocardial infarction, stroke, or reperfusion injury; autoimmune disorders, e.g., systemic lupus erythematosus, or immune-mediated glomerulonephritis; or profilerative disorders, e.g., cancer, such as follicular lymphomas, carcinomas with p53 mutations, or hormone-dependent tumors, e.g., breast cancer, prostate cancer, or ovarian cancer). Clinical manifestations of faulty apoptosis are also seen in stroke and in rheumatoid arthritis. Wilson (1998) *Biochem. Cell. Biol.* 76:573–582.

Failure to remove autoimmune cells that arise during development or that develop as a result of somatic mutation during an immune response can result in autoimmune disease. One of the molecules that plays a critical role in regulating cell death in lymphocytes is the cell surface receptor for Fas.

Viral infections, such as those caused by herpesviruses, poxviruses, and adenoviruses, may result in aberrant apoptosis. Populations of cells are often depleted in the event of viral infection, with perhaps the most dramatic example being the cell depletion caused by the human immunodeficiency virus (HIV). Most T cells that die during HIV infections do not appear to be infected with HIV. Stimulation of the CD4 receptor may result in the enhanced susceptibility of uninfected T cells to undergo apoptosis.

Many disorders can be classified based on whether they are associated with abnormally high or abnormally low apoptosis. Thompson (1995) *Science* 267:1456–1462. Apoptosis may be involved in acute trauma, myocardial infarction, stroke, and infectious diseases, such as viral hepatitis and acquired immunodeficiency syndrome.

Primary apoptosis deficiencies include graft rejection. Accordingly, the invention is relevant to the identification of genes useful in inhibiting graft rejection.

Primary apoptosis deficiencies also include autoimmune diabetes. Accordingly, the invention is relevant to genes involved in autoimmune diabetes and accordingly, to the identification of agents that act on these targets to modulate the expression of these genes and hence, to treat or diagnose this disorder. Further, it has been suggested that all autoimmune disorders can be viewed as primary deficiencies of apoptosis (Hetts, above). Accordingly, the invention is relevant for screening for gene expression and transcriptional profiling in any autoimmune disorder and for screening for agents that affect the expression or transcriptional profile of the kinase genes.

Primary apoptosis deficiencies also include local self reactive disorder. This includes Hashimoto thyroiditis.

Primary apoptosis deficiencies also include lymphoproliferation and autoimmunity. This includes, but is not limited to, Canale-Smith syndrome.

Primary apoptosis deficiencies also include cancer. For example, p53 induces apoptosis by acting as a transcription factor that activates expression of various apoptosis-mediating genes or by upregulating apoptosis-mediating genes such as Bax.

Primary apoptosis excesses are associated with neurodegenerative disorders including Alzheimer's disease, Parkinson's disease, spinal muscular atrophy, and amyotrophic lateral sclerosis.

Primary apoptosis excesses are also associated with heart disease including idiopathic dilated cardiomyopathy, ischemic cardiomyopathy, and valvular heart disease. Evidence has also been shown of apoptosis in heart failure resulting from arrhythmogenic right ventricular dysplasia. For all these disorders, see Hetts, above.

Death receptors also include the TNF receptor-1 and hence, TNF acts as a death ligand.

A wide variety of neurological diseases are characterized by the gradual loss of specific sets of neurons. Such disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death.

In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow.

These disorders could result from the activation of genes that promote apoptosis, acquired deficiencies in stromal cells or hematopoietic survival factors, or the direct effects of toxins and mediators of immune responses.

Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis.

The invention also pertains to disorders of the central nervous system (CNS). These disorders include, but are not limited to cognitive and neurodegenerative disorders such as Alzheimer's disease, senile dementia, Huntington's disease, amyotrophic lateral sclerosis, and Parkinson's disease, as well as Gilles de la Tourette's syndrome, autonomic function disorders such as hypertension and sleep disorders, and neuropsychiatric disorders that include, but are not limited to schizophrenia, schizoaffective disorder, attention deficit disorder, dysthymic disorder, major depressive disorder, mania, obsessive-compulsive disorder, psychoactive substance use disorders, anxiety, panic disorder, as well as bipolar affective disorder, e.g., severe bipolar affective (mood) disorder (BP-I), bipolar affective (mood) disorder with hypomania and major depression (BP-II). Further CNS-related disorders include, for example, those listed in the American Psychiatric Association's Diagnostic and Statistical manual of Mental Disorders (DSM), the most current version of which is incorporated herein by reference in its entirety.

As used herein, "differential expression" or "differentially expressed" includes both quantative and qualitative differences in the temporal and/or cellular expression pattern of a gene, e.g., the protein kinase gene disclosed herein, among, for example, normal cells and cells undergoing programmed cell death. Genes which are differentially expressed can be used as part of a prognostic or diagnostic marker for the evaluation of subjects at risk for developing a disorder characterized by deregulated programmed cell death. Depending on the expression level of the gene, the progression state of the disorder can also be evaluated.

The present invention is based, at least in part, on the identification of a novel kinase protein and nucleic acid molecule, that comprises a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence identity as defined herein. Such family members can be naturally or non-naturally occurring and can be from either the same or different species. For example, a family can contain a first protein of human origin, as well as other, distinct proteins of human origin or alternatively, can contain homologs of non-human origin. Members of a family may also have common functional characteristics.

One embodiment of the invention features a protein kinase nucleic acid molecule, preferably a human protein kinase molecule, identified based on a consensus motif or protein domain characteristic of a protein kinase family of proteins, specifically, a serine/threonine protein kinase also containing ankyrin function.

Eukaryotic Protein Kinase Nucleic Acid and Polypeptide Molecules

In one embodiment, the isolated nucleic acid molecule of the present invention encodes a eukaryotic protein kinase polypeptide. Eukaryotic protein kinases (described in, for example, Hanks et al. (1995) *FASEB J.* 9:576–596) are enzymes that belong to an extensive family of proteins that share a conserved catalytic core common to both serine/threonine and tyrosine protein kinases. There are a number of conserved regions in the catalytic domain of protein kinases. One of these regions, located in the N-terminal extremity of the catalytic domain, is a glycine-rich stretch of residues in the vicinity of a lysine residue, which has been shown to be involved in ATP binding. Another region, located in the central part of the catalytic domain, contains a conserved aspartic acid residue which is important for the catalytic activity of the enzyme (Knighton et al. (1991) *Science* 253:407–414). Two signature patterns have been described for this region: one specific for serine/threonine kinases and one for tyrosine kinases.

Eukaryotic protein kinase polypeptides can include one of the following consensus sequences:

[LIV]-G-{P}-G-{P}-[FYWMGSTNH]-[SGA]-{PW}-[LIVCAT]-{PD}-x[GSTACLIVMFY]-x(5,18)-[LIVMFYWCSTAR]-[AIVP]-[LIVMFAGCKR]-K [K binds ATP]

[LIVMFYC]-x-[HY]-x-D-[LIVMFY]-K-x(2)-N-[LIVMFYCT](3) [D is an active site residue]

[LIVMFYC]-x-[HY]-x-D-[LIVMFY]-[RSTAC]-x(2)-N-[LIVMFYC](3) [D is an active site residue]

Novel Protein Kinase Sequence

The protein kinase gene of the invention was identified in a human primary osteoblast cDNA library. The 14171 clone set forth in SEQ ID NO:1 is approximately 3860 nucleotides and comprises a corresponding cDNA sequence set forth in SEQ ID NO:3. This transcript has a nucleotide open reading frame encoding an amino acid of about 784 amino acids, set forth in SEQ ID NO:2. The coding sequence for 14171 is shown in SEQ ID NO:3.

Preferred kinase polypeptides of the present invention have an amino acid sequence sufficiently identical to the amino acid sequence of SEQ ID NO:2 or a domain thereof. The term "sufficiently identical" is used herein to refer to a first amino acid or nucleotide sequence that contains a sufficient or minimum number of identical or equivalent (e.g., with a similar side chain) amino acid residues or nucleotides to a second amino acid or nucleotide sequence such that the first and second amino acid or nucleotide sequences have a common structural domain and/or common functional activity. For example, amino acid or nucleotide sequences that contain a common structural domain having at least about 60%, 65%, 70%, 75%, 80%, 85%, 90%, 95%, 96%, 97%, 98%, or 99% identity are defined herein as sufficiently identical.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (1970) *J. Mol. Biol.* 48:444–453 algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. A particularly preferred set of parameters (and the one that should be used if the practitioner is uncertain about what parameters should be applied to determine if a molecule is within a sequence identity or homology limitation of the invention) is using a Blossum 62 scoring matrix with a gap open penalty of 12, a gap extend penalty of 4, and a frameshift gap penalty of 5.

The percent identity between two amino acid or nucleotide sequences can be determined using the algorithm of E. Meyers and W. Miller (1989) *CABIOS* 4:11–17 which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403–10. BLAST nucleotide searches can be performed with the NBLAST program, score=100, wordlength=12 to obtain nucleotide sequences homologous to 14171 protein kinase nucleic acid molecules of the invention. BLAST protein searches can be performed with the XBLAST program, score=50, wordlength=3 to obtain amino acid sequences homologous to 14171 protein kinase protein molecules of the invention. To obtain gapped alignments for comparison purposes, Gapped BLAST can be utilized as described in Altschul et al. (1997) *Nucleic Acids Res.* 25(17):3389–3402. When utilizing BLAST and Gapped BLAST programs, the default parameters of the respective programs (e.g., XBLAST and NBLAST) can be used. See http://www.ncbi.nlm.nih.gov.

Figure 4:
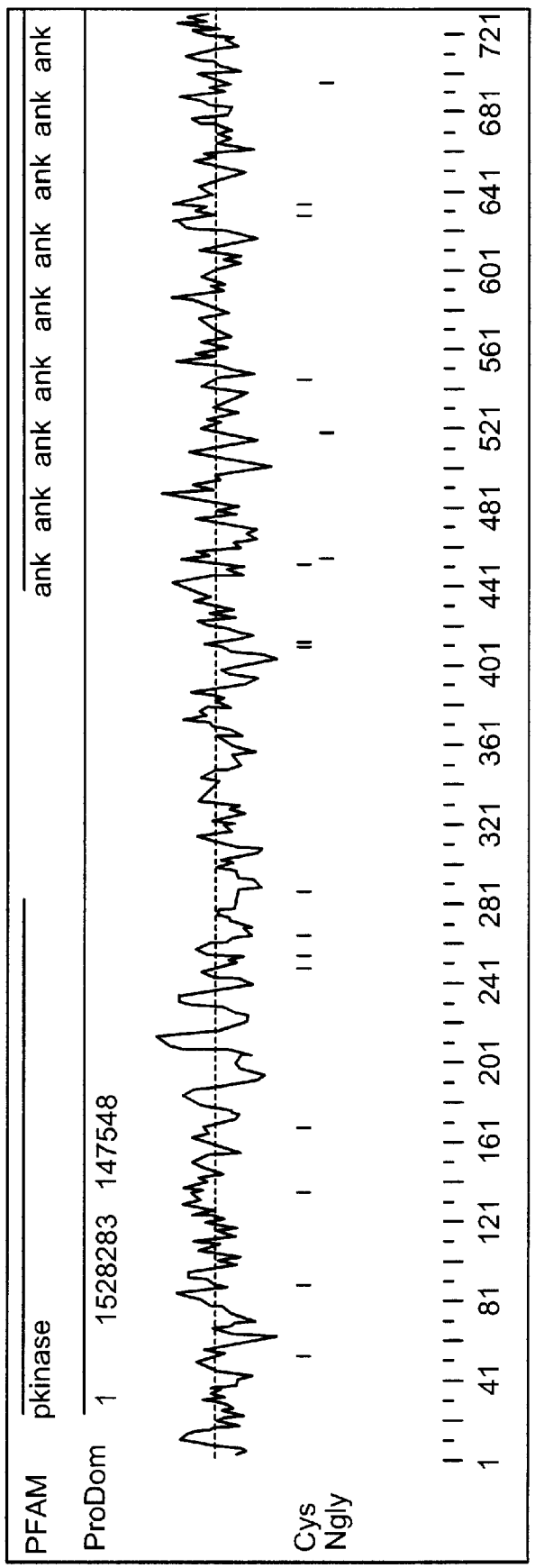
FIG. 4 shows a 14171 hydrophobicity plot. The plot shows that the 14171 protein kinase contains a kinase domain at the 5' end and 6 ankyrin repeats at the 3' end. Relative hydrophobic residues are shown above the dashed horizontal line, and relative hydrophilic residues are below the dashed horizontal line. The cysteine residues (cys) and N glycosylation sites (Ngly) are indicated by short vertical lines just below the hydropathy trace. The numbers corresponding to the amino acid sequence (shown in SEQ ID NO:2) of human 14171 protein kinase are indicated. Polypeptides of the invention include fragments which include: all or a part of a hydrophobic sequence (a sequence above the dashed line); or all or a part of a hydrophilic fragment (a sequence below the dashed line). Other fragments include a cysteine residue or a N-glycosylation site.

Accordingly, another embodiment of the invention features isolated protein kinase proteins and polypeptides having a protein kinase protein activity. As used interchangeably herein, a "protein kinase protein activity", "biological activity of a protein kinase protein", or "functional activity of a protein kinase protein" refers to an activity exerted by a protein kinase protein, polypeptide, or nucleic acid molecule on a protein kinase-responsive cell as determined in vivo, or in vitro, according to standard assay techniques. A protein kinase activity can be a direct activity, such as an association with or an enzymatic activity on a second protein, such as on nuclear factor-κB or Jun N-terminal kinase, or an indirect activity, such as a cellular signaling activity mediated by interaction of the protein kinase protein with a second protein, such as the induction of cellular signals resulting in cell growth, differentiation, and death that is mediated by members of the tumor necrosis factor receptor superfamily, for example, as discussed hereinabove. In a preferred embodiment, a protein kinase activity includes at least one or more of the following activities: (1) modulating (stimulating and/or enhancing or inhibiting) cellular proliferation, growth and/or metabolism (e.g. in those cells in which the sequence is expressed, including virus-infected cells); (2) the regulation of transmission of signals from cellular receptors, e.g., growth factor receptors; (3) the modulation of the entry of cells into mitosis; (4) the modulation of cellular differentiation; (5) the modulation of cell death; and (6) the regulation of cytoskeleton function, e.g., actin bundling. Functions also include, but are not limited to, those shown for the specific functional sites in FIG. 4, including ATP binding and ankyrin function.

An "isolated" or "purified" protein kinase nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein-encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated kinase nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A kinase protein that is substantially free of cellular material includes preparations of kinase protein having less than about 30%, 20%, 10%, or 5% (by dry weight) of non-kinase protein (also referred to herein as a "contaminating protein"). When the kinase protein or biologically active portion thereof is recombinantly produced, preferably, culture medium represents less than about 30%, 20%, 10%, or 5% of the volume of the protein preparation. When kinase protein is produced by chemical synthesis, preferably the protein preparations have less than about 30%, 20%, 10%, or 5% (by dry weight) of chemical precursors or non-kinase chemicals.

Various aspects of the invention are described in further detail in the following subsections.

I. Isolated Nucleic Acid Molecules

One aspect of the invention pertains to an isolated nucleic acid molecule comprising a nucleotide sequence encoding a protein kinase protein or biologically active portion thereof, as well as a nucleic acid molecule sufficient for use as a hybridization probe to identify kinase-encoding nucleic acids (e.g., the kinase mRNA) and fragments for use as PCR primers for the amplification or mutation of kinase nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA. A nucleotide sequence encoding the kinase proteins of the present invention includes the sequences set forth in SEQ ID NO:1, SEQ ID NO:3, and the complements thereof. By "complement" is intended a nucleotide sequence that is sufficiently complementary to a given nucleotide sequence such that it can hybridize to the given nucleotide sequence to thereby form a stable duplex. The corresponding amino acid sequence for the kinase protein encoded by the nucleotide sequence is set forth in SEQ ID NO:2.

Nucleic acid molecules that are fragments of the kinase nucleotide sequence are also encompassed by the present invention. By "fragment" is intended a portion of the nucleotide sequence encoding a kinase protein of the invention. A fragment of a kinase nucleotide sequence may encode a biologically active portion of a kinase protein, or it may be a fragment that can be used as a hybridization probe or PCR primer using methods disclosed below. A biologically active portion of the kinase protein can be prepared by isolating a portion of the kinase nucleotide sequence of the invention, expressing the encoded portion of the kinase protein (e.g., by recombinant expression in vitro), and assessing the activity of the encoded portion of the kinase protein. Generally, nucleic acid molecules that are fragments of a protein kinase nucleotide sequence comprise at least 15, 20, 50, 75, 100, 325, 350, 375, 400, 425, 450, 500, 550, 600, 650, 700, 750, 800, 850, 900, 950, 1000, 1100, 1200, 1300, 1400, 1500, 1600, 1700, 1800, 1900, 2000, 2100, 2200, 2300,2400, 2500, 2600, 2700, 2800, 2900, 3000, 3100, 3200, 3300, 3400, 3500, 3600, 3700, 3800, or up to 3860 nucleotides present in the nucleotide sequence disclosed herein. Alternatively, a nucleic acid molecule that is a fragment of a 14171-like nucleotide sequence of the present invention comprises a nucleotide sequence consisting of nucleotides 1–100, 100–200, 200–300, 300–400, 400–500, 500–600, 600–700, 700–800, 800–900, 900–1000, 1000–1100, 1100–1200, 1200–1300, 1300–1400, 1400–1500, 1500–1600, 1600–1700, 1700–1800, 1800–1900, 1900–2000, 2000–2100, 2100–2200, 2200–2300, 2300–2400, 2400–2500, 2500–2600, 2600–2700, 2700–2800, 2800–2900, 2900–3000, 3000–3100, 3100–3200, 3200–3300, 3300–3400, 3400–3500, 3500–3600, 3600–3700, 3700–3800, 3800–3860 of SEQ ID NO:1.

It is understood that isolated fragments include any contiguous sequence not disclosed prior to the invention as well as sequences that are substantially the same and which are not disclosed. Accordingly, if a fragment is disclosed prior to the present invention, that fragment is not intended to be encompassed by the invention. When a sequence is not disclosed prior to the present invention, an isolated nucleic acid fragment is at least about 12, 15, 20, 25, or 30 contiguous nucleotides. Other regions of the nucleotide sequence may comprise fragments of various sizes, depending upon potential homology with previously disclosed sequences. Further, the sizes of the fragments may vary depending on the region analyzed. In the present case, fragments can include as few as 5–10, or 10–20 nucleotides from nucleotide 1-approximately 962, and approximately 1700-approximately 2518. Similarly, amino acid fragments encompassed by these regions can include as few as 4–10, 10–15, 15–20, 20–30, and 30–40 amino acids.

Generally, a fragment of a kinase nucleotide sequence that encodes a biologically active portion of a kinase protein of the invention will encode at least 15, 25, 30, 50, 75, 100, 125, 150, 160, or 170 contiguous amino acids, or up to the total number of amino acids present in a full-length kinase protein of the invention. Fragments of a kinase nucleotide sequence that are useful as hybridization probes for PCR primers generally need not encode a biologically active portion of a kinase protein.

Nucleic acid molecules that are variants of the kinase nucleotide sequence disclosed herein are also encompassed by the present invention. "Variants" of the kinase nucleotide sequence include those sequences that retain the biological activity of the protein kinase set forth in SEQ ID NO:2 but that differ conservatively because of the degeneracy of the genetic code. These naturally-occurring allelic variants can be identified with the use of well-known molecular biology techniques, such as polymerase chain reaction (PCR) and hybridization techniques as outlined below. Variant nucleotide sequences also include synthetically-derived nucleotide sequences that have been generated, for example, by using site-directed mutagenesis but which still encode the kinase protein disclosed in the present invention as discussed below. Generally, nucleotide sequence variants of the invention will have at least 60%, 65%, 70%, 75%, 80%, 85%, 90%, 91%, 92%, 93%, 94%, 95%, 96%, 97%, 98%, or 99% identity nucleotide sequence disclosed herein. A variant kinase nucleotide sequence will encode a protein kinase that has the amino acid sequence having at least 60%, 65%, 70%, 75%, 80%, 85%, 90%, 91%, 92%, 93%, 94%, 95%, 96%, 97%, 98%, or 99% identity amino acid sequence of the protein kinase disclosed herein and retains the biological activity of the protein kinase.

In addition to the kinase nucleotide sequence shown in SEQ ID NO: 1, it will be appreciated by those skilled in the art that DNA sequence polymorphisms that lead to changes in the amino acid sequences of the kinase protein may exist within a population (e.g., the human population). Such genetic polymorphism in a protein kinase gene of the invention may exist among individuals within a population due to natural allelic variation. An allele is one of a group of genes that occur alternatively at a given genetic locus. As used herein, the terms "gene" and "recombinant gene" refer to nucleic acid molecules comprising an open reading frame encoding a protein kinase protein, preferably a mammalian protein kinase protein. As used herein, the phrase "allelic variant" refers to a nucleotide sequence that occurs at a protein kinase locus or to a polypeptide encoded by the nucleotide sequence. Such natural allelic variations can typically result in 1–5% variance in the nucleotide sequence of the kinase gene. Any and all such nucleotide variations and resulting amino acid polymorphisms or variations in a kinase sequence that are the result of natural allelic variation and that do not alter the functional activity of kinase proteins are intended to be within the scope of the invention.

Moreover, nucleic acid molecules encoding kinase protein from other species (kinase homologs), which have a nucleotide sequence differing from that of the kinase sequence disclosed herein, are intended to be within the scope of the invention. Nucleic acid molecules corresponding to natural allelic variants and homologs of the kinase cDNA of the invention can be isolated based on their identity to the kinase nucleic acid disclosed herein using the cDNA, or a portion thereof, as a hybridization probe according to standard hybridization techniques under stringent hybridization conditions as disclosed below.

In addition to naturally-occurring allelic variants of the kinase sequence that may exist in the population, the skilled artisan will further appreciate that changes can be introduced by mutation into the nucleotide sequences of the invention thereby leading to changes in the amino acid sequence of the encoded kinase protein, without altering the biological activity of the kinase protein. Thus, an isolated nucleic acid molecule encoding a protein kinase protein having a sequence that differs from that of SEQ ID NO:2 can be created by introducing one or more nucleotide substitutions, additions, or deletions into the nucleotide sequences disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably, conservative amino acid substitutions may be made at one or more predicted, preferably nonessential amino acid residues. A "nonessential" amino acid residue is a residue that can be altered from the wild-type sequence of a protein kinase protein (e.g., the sequence of SEQ ID NO:2) without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Such substitutions would not be made for conserved amino acid residues or for amino acid residues residing within a conserved protein domain, such as the serine/threonine protein kinase domain of the disclosed clones, where such residues are essential for protein activity.

Alternatively, variant kinase nucleotide sequences can be made by introducing mutations randomly along all or part of the kinase coding sequence, such as by saturation mutagenesis, and the resultant mutants can be screened for kinase biological activity to identify mutants that retain activity. Following mutagenesis, the encoded protein can be expressed recombinantly, and the activity of the protein can be determined using standard assay techniques.

Thus the nucleotide sequence of the invention includes the sequence disclosed herein as well as fragments and variants thereof The kinase nucleotide sequence of the invention, and fragments and variants thereof, can be used as a probe and/or primer to identify and/or clone kinase homologs in other cell types, e.g., from other tissues, as well as kinase homologs from other mammals. Such probes can be used to detect transcripts or genomic sequences encoding the same or identical proteins. These probes can be used as part of a diagnostic test kit for identifying cells or tissues that misexpress a kinase protein, such as by measuring levels of a kinase-encoding nucleic acid in a sample of cells from a subject, e.g., detecting kinase mRNA levels or determining whether a genomic kinase gene has been mutated or deleted.

In this manner, methods such as PCR, hybridization, and the like can be used to identify such sequences having substantial identity to the sequences of the invention. See, for example, Sambrook et al. (1989) *Molecular Cloning: Laboratory Manual* (2d ed., Cold Spring Harbor Laboratory Press, Plainview, N.Y.) and Innis, et al. (1990) *PCR Protocols: A Guide to Methods and Applications* (Academic Press, NY). Kinase nucleotide sequences isolated based on their sequence identity to the kinase nucleotide sequence set forth herein or to fragments and variants thereof are encompassed by the present invention.

In a hybridization method, all or part of a known kinase nucleotide sequence can be used to screen cDNA or genomic libraries. Methods for construction of such cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.). The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known kinase nucleotide sequences disclosed herein. Degenerate primers designed on the basis of conserved nucleotides or amino acid residues in a known kinase nucleotide sequence or encoded amino acid sequence can additionally be used. The probe typically comprises a region of nucleotide sequence that hybridizes under stringent conditions to at least about 12, preferably about 25, more preferably about 50, 75, 100, 125, 150, 175, 200, 250, 300, 350, or 400 consecutive nucleotides of a kinase nucleotide sequence of the invention or a fragment or variant thereof. Preparation of probes for hybridization is generally known in the art and is disclosed in Sambrook et al. (1989) *Molecular Cloning: A Laboratory Manual* (2d ed., Cold Spring Harbor Laboratory Press, Plainview, N.Y.), herein incorporated by reference.

For example, in one embodiment, a previously unidentified kinase nucleic acid molecule hybridizes under stringent conditions to a probe that is a nucleic acid molecule comprising the kinase nucleotide sequence of the invention or a fragment thereof. In another embodiment, the previously unknown kinase nucleic acid molecule is at least 300, 325, 350, 375, 400, 425, 450, 500, 550, 600, 650, 700, 800, 900, 1000, 2,000, 3,000, or 4,000 nucleotides in length and hybridizes under stringent conditions to a probe that is a nucleic acid molecule comprising the kinase nucleotide sequence disclosed herein or a fragment thereof.

Accordingly, in another embodiment, an isolated previously unknown kinase nucleic acid molecule of the invention is at least 300, 325, 350, 375, 400, 425, 450, 500, 518, 550, 600, 650, 700, 800, 831, 900, 981, 1000, 1,100, 1,200, 1,300, 1,400, 1,500, 1,600, 1,700, 1,800, 1,900, 2,000, or 2,060 nucleotides in length and hybridizes under stringent conditions to a probe that is a nucleic acid molecule comprising one of the nucleotide sequences of the invention, preferably the coding sequence set forth in SEQ ID NO:1 or a complement, fragment, or variant thereof.

As used herein, the term "hybridizes under stringent conditions" is intended to describe conditions for hybridization and washing. Stringent conditions are known to those skilled in the art and can be found in *Current Protocols in Molecular Biology* John Wiley & Sons, N.Y. (1989), 6.3.1–6.3.6. Aqueous and nonaqueous methods are described in that reference and either can be used. A preferred, example of stringent hybridization conditions are hybridization in 6×sodium chloride/sodium citrate (SSC) at about 45° C., followed by one or more washes in 0.2×SSC, 0.1% SDS at 50° C. Another example of stringent hybridization conditions are hybridization in 6×sodium chloride/sodium citrate (SSC) at about 45° C., followed by one or more washes in 0.2×SSC, 0.1% SDS at 55° C. A further example of stringent hybridization conditions are hybridization in 6×sodium chloride/sodium citrate (SSC) at about 45° C., followed by one or more washes in 0.2×SSC, 0.1% SDS at 60° C. Preferably, stringent hybridization conditions are hybridization in 6×sodium chloride/sodium citrate (SSC) at about 45'.C, followed by one or more washes in 0.2×SSC, 0.1% SDS at 65° C. Particularly preferred stringency conditions (and the conditions that should be used if the practitioner is uncertain about what conditions should be applied to determine if a molecule is within a hybridization limitation of the invention) are 0.5M Sodium Phosphate, 7% SDS at 65° C., followed by one or more washes at 0.2×SSC, 1% SDS at 65° C. Preferably, an isolated nucleic acid molecule of the invention that hybridizes under stringent conditions to the sequence of SEQ ID NO:1, or SEQ ID NO:3, corresponds to a naturally-occurring nucleic acid molecule.

As used herein, a "naturally-occurring" nucleic acid molecule refers to an RNA or DNA molecule having a nucleotide sequence that occurs in nature (e.g., encodes a natural protein).

Thus, in addition to the kinase nucleotide sequence disclosed herein and fragments and variants thereof, the isolated nucleic acid molecule of the invention also encompasses homologous DNA sequences identified and isolated from other cells and/or organisms by hybridization with entire or partial sequences obtained from the kinase nucleotide sequence disclosed herein or variants and fragments thereof.

As used herein, "heterologous" in reference to a polypeptide or amino acid sequence is a polypeptide or amino acid sequence that originates from a foreign protein, or, if from the same protein, is substantially modified from its native form in composition by deliberate human intervention. A heterologous protein may originate from a foreign species, or, if from the same species, is substantially modified from its original form by deliberate human intervention.

The present invention also encompasses antisense nucleic acid molecules, i.e., molecules that are complementary to a sense nucleic acid encoding a protein, e.g., complementary to the coding strand of a double-stranded cDNA molecule, or complementary to an mRNA sequence. Accordingly, an antisense nucleic acid can hydrogen bond to a sense nucleic acid. The antisense nucleic acid can be complementary to an entire kinase coding strand, or to only a portion thereof, e.g., all or part of the protein coding region (or open reading frame). An antisense nucleic acid molecule can be antisense to a noncoding region of the coding strand of a nucleotide sequence encoding a kinase protein. The noncoding regions are the 5' and 3' sequences that flank the coding region and are not translated into amino acids.

Given the coding-strand sequence encoding the kinase protein disclosed herein (e.g., SEQ ID NO:1), antisense nucleic acids of the invention can be designed according to the rules of Watson and Crick base pairing. The antisense nucleic acid molecule can be complementary to the entire coding region of kinase mRNA, but more preferably is an oligonucleotide that is antisense to only a portion of the coding or noncoding region of kinase mRNA. For example, the antisense oligonucleotide can be complementary to the region surrounding the translation start site of kinase mRNA. An antisense oligonucleotide can be, for example, about 5, 10, 15, 20, 25, 30, 35, 40, 45, or 50 nucleotides in length. An antisense nucleic acid of the invention can be constructed using chemical synthesis and enzymatic ligation procedures known in the art.

For example, an antisense nucleic acid (e.g., an antisense oligonucleotide) can be chemically synthesized using naturally-occurring nucleotides or variously modified nucleotides designed to increase the biological stability of the molecules or to increase the physical stability of the duplex formed between the antisense and sense nucleic acids, including, but not limited to, for example, phosphorothioate derivatives and acridine substituted nucleotides. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

The antisense nucleic acid molecules of the invention are typically administered to a subject or generated in situ such that they hybridize with or bind to cellular mRNA and/or genomic DNA encoding a kinase protein to thereby inhibit expression of the protein, e.g., by inhibiting transcription and/or translation. An example of a route of administration of antisense nucleic acid molecules of the invention includes direct injection at a tissue site. Alternatively, antisense nucleic acid molecules can be modified to target selected cells and then administered systemically. For example, antisense molecules can be linked to peptides or antibodies to form a complex that specifically binds to receptors or antigens expressed on a selected cell surface. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the invention can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res.* 15:6625–6641). The antisense nucleic acid molecule can also comprise a 2'-o-methylribonucleotide (Inoue et al. (1987) *Nucleic Acids Res.* 15:6131–6148) or a chimeric RNA-DNA analogue (Inoue et al. (1987) *FEBS Lett.* 215:327–330).

The invention also encompasses ribozymes, which are catalytic RNA molecules with ribonuclease activity that are capable of cleaving a single-stranded nucleic acid, such as an mRNA, to which they have a complementary region. Ribozymes (e.g., hammerhead ribozymes (described in Haselhoff and Gerlach (1988) *Nature* 334:585–591)) can be used to catalytically cleave kinase mRNA transcripts to thereby inhibit translation of kinase mRNA. A ribozyme having specificity for a kinase-encoding nucleic acid can be designed based upon the nucleotide sequence of a kinase cDNA disclosed herein (e.g., SEQ ID NO:1). See, e.g., Cech et al., U.S. Pat. No. 4,987,071; and Cech et al, U.S. Pat. No. 5,116,742. Alternatively, kinase mRNA can be used to select a catalytic RNA having a specific ribonuclease activity from a pool of RNA molecules. See, e.g., Bartel and Szostak (1993) *Science* 261:1411–1418.

The invention also encompasses nucleic acid molecules that form triple helical structures. For example, kinase gene expression can be inhibited by targeting nucleotide sequences complementary to the regulatory region of the kinase protein (e.g., the kinase promoter and/or enhancers) to form triple helical structures that prevent transcription of the kinase gene in target cells. See generally Helene (1991) *Anticancer Drug Des.* 6(6):569; Helene (1992) *Ann. N.Y. Acad. Sci.* 660:27; and Maher (1992) *Bioassays* 14(12):807.

In preferred embodiments, the nucleic acid molecules of the invention can be modified at the base moiety, sugar moiety, or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorganic & Medicinal Chemistry* 4:5). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid-phase peptide synthesis protocols as described in Hyrup et al. (1996), supra; Perry-O'Keefe et al. (1996) *Proc. Natl. Acad. Sci. USA* 93:14670.

PNAs of a kinase molecule can be used in therapeutic and diagnostic applications. For example, PNAs can be used as antisense or antigen agents for sequence-specific modulation of gene expression by, e.g., inducing transcription or translation arrest or inhibiting replication. PNAs of the invention can also be used, e.g., in the analysis of single base pair mutations in a gene by, e.g., PNA-directed PCR clamping, as artificial restriction enzymes when used in combination with other enzymes, e.g., S1 nucleases (Hyrup (1996), supra, or as probes or primers for DNA sequence and hybridization (Hyrup (1996), supra; Perry-O'Keefe et al. (1996), supra).

In another embodiment, PNAs of a kinase molecule can be modified, e.g., to enhance their stability, specificity, or cellular uptake, by attaching lipophilic or other helper groups to PNA, by the formation of PNA-DNA chimeras, or by the use of liposomes or other techniques of drug delivery known in the art. The synthesis of PNA-DNA chimeras can be performed as described in Hyrup (1996), supra; Finn et al. (1996) *Nucleic Acids Res.* 24(17):3357–63; Mag et al. (1989) *Nucleic Acids Res.* 17:5973; and Peterser et al. (1975) *Bioorganic Med. Chem. Lett.* 5:1119.

II. Isolated Protein Kinase Proteins and Anti-protein Kinase Antibodies

Protein kinase proteins are also encompassed within the present invention. The invention encompasses a protein having the amino acid sequence set forth in SEQ ID NO:2, fragments, and variants thereof that retain the biological activity of the protein kinase.

"Fragments" or "biologically active portions" include polypeptide fragments suitable for use as immunogens to raise anti-kinase antibodies. Fragments include peptides comprising amino acid sequences sufficiently identical to or derived from the amino acid sequences of a kinase protein of the invention and exhibiting at least one activity of a kinase protein, but which include fewer amino acids than the full-length kinase protein disclosed herein. Typically, biologically active portions comprise a domain or motif with at least one activity of the kinase protein. A biologically active portion of a kinase protein can be a polypeptide which is, for example, 10, 25, 50, 100 or more amino acids in length. Such biologically active portions can be prepared by recombinant techniques and evaluated for one or more of the functional activities of a native kinase protein.

By "variants" is intended proteins or polypeptides having an amino acid sequence that is at least about 60%, 65%, 70%, preferably about 75%, 85%, 95%, or 98% identical to the amino acid sequence of SEQ ID NO:2. Variants also include polypeptides encoded by a nucleic acid molecule that hybridizes to the nucleic acid molecule of SEQ ID NO:1, SEQ ID NO:3, or a complement thereof, under stringent conditions. Variants retain the biological activity (e.g. the protein kinase activity) of the polypeptide set forth in SEQ ID NO:2. In another embodiment, a variant of an isolated polypeptide of the present invention differs, by at least 1, but less than 5, 10, 20, 50, or 100 amino acid residues from the sequence shown in SEQ ID NO:2. If alignment is needed for this comparison the sequences should be aligned for maximum identity. "Looped" out sequences from deletions or insertions, or mismatches, are considered differences. Such variants retain the functional activity of the kinase proteins of the invention. Variants include polypeptides that differ in amino acid sequence due to natural allelic variation or mutagenesis.

The invention also provides kinase chimeric or fusion proteins. As used herein, a kinase "chimeric protein" or "fusion protein" comprises a kinase polypeptide operably linked to a non-kinase polypeptide. A "kinase polypeptide" refers to a polypeptide having an amino acid sequence corresponding to a kinase protein, whereas a "non-kinase polypeptide" refers to a polypeptide having an amino acid sequence corresponding to a protein that is not substantially identical to the kinase protein, e.g., a protein that is different from the kinase protein and which is derived from the same or a different organism. Within a kinase fusion protein, the kinase polypeptide can correspond to all or a portion of a kinase protein, preferably at least one biologically active portion of a kinase protein. Within the fusion protein, the term "operably linked" is intended to indicate that the kinase polypeptide and the non-kinase polypeptide are fused in-frame to each other. The non-kinase polypeptide can be fused to the N-terminus or C-terminus of the kinase polypeptide.

One useful fusion protein is a GST-kinase fusion protein in which the kinase sequences are fused to the C-terminus of the GST sequences. Such fusion proteins can facilitate the purification of recombinant kinase proteins.

In yet another embodiment, the fusion protein is a kinase-immunoglobulin fusion protein in which all or part of a kinase protein is fused to sequences derived from a member of the immunoglobulin protein family. The kinase-immunoglobulin fusion proteins of the invention can be incorporated into pharmaceutical compositions and administered to a subject to inhibit an interaction between a kinase ligand and a kinase protein on the surface of a cell, thereby suppressing kinase-mediated signal transduction in vivo. The kinase-immunoglobulin fusion proteins can be used to affect the bioavailability of a kinase cognate ligand. Inhibition of the kinase ligand/kinase interaction may be useful therapeutically, both for treating proliferative and differentiative disorders and for modulating (e.g., promoting or inhibiting) cell survival. Moreover, the kinase-immunoglobulin fusion proteins of the invention can be used as immunogens to produce anti-kinase antibodies in a subject, to purify kinase ligands, and in screening assays to identify molecules that inhibit the interaction of a kinase protein with a kinase ligand.

Preferably, a kinase chimeric or fusion protein of the invention is produced by standard recombinant DNA techniques. For example, DNA fragments coding for the different polypeptide sequences may be ligated together in-frame, or the fusion gene can be synthesized, such as with automated DNA synthesizers. Alternatively, PCR amplification of gene fragments can be carried out using anchor primers that give rise to complementary overhangs between two consecutive gene fragments, which can subsequently be annealed and reamplified to generate a chimeric gene sequence (see, e.g., Ausubel et al., eds. (1995) *Current Protocols in Molecular Biology*) (Greene Publishing and Wiley-Interscience, NY). Moreover, a kinase-encoding nucleic acid can be cloned into a commercially available expression vector such that it is linked in-frame to an existing fusion moiety. Variants of the kinase proteins can function as either kinase agonists (mimetics) or as kinase antagonists. Variants of the kinase protein can be generated by mutagenesis, e.g., discrete point mutation or truncation of the kinase protein. An agonist of the kinase protein can retain substantially the same or a subset of the biological activities of the naturally-occurring form of the kinase protein. An antagonist of the kinase protein can inhibit one or more of the activities of the naturally-occurring form of the kinase protein by, for example, competitively binding to a downstream or upstream member of a cellular signaling cascade that includes the kinase protein. Thus, specific biological effects can be elicited by treatment with a variant of limited function. Treatment of a subject with a variant having a subset of the biological activities of the naturally-occurring form of the protein can have fewer side effects in a subject relative to treatment with the naturally occurring form of the kinase proteins.

Variants of the kinase protein that function as either kinase agonists or as kinase antagonists can be identified by screening combinatorial libraries of mutants, e.g., truncation mutants, of the kinase protein for kinase protein agonist or antagonist activity. In one embodiment, a variegated library of kinase variants is generated by combinatorial mutagenesis at the nucleic acid level and is encoded by a variegated gene library. A variegated library of kinase variants can be produced by, for example, enzymatically ligating a mixture of synthetic oligonucleotides into gene sequences such that a degenerate set of potential kinase sequences is expressible as individual polypeptides, or alternatively, as a set of larger fusion proteins (e.g., for phage display) containing the set of kinase sequences therein. There are a variety of methods that can be used to produce libraries of potential kinase variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential kinase sequences. Methods for synthesizing degenerate oligonucleotides are known in the art (see, e.g., Narang (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477).

In addition, libraries of fragments of the kinase protein coding sequence can be used to generate a variegated population of kinase fragments for screening and subsequent selection of variants of a kinase protein. In one embodiment, a library of coding sequence fragments can be generated by treating a double-stranded PCR fragment of a kinase coding sequence with a nuclease under conditions wherein nicking occurs only about once per molecule, denaturing the double-stranded DNA, renaturing the DNA to form double-stranded DNA which can include sense/antisense pairs from different nicked products, removing single-stranded portions from reformed duplexes by treatment with S1 nuclease, and ligating the resulting fragment library into an expression vector. By this method, one can derive an expression library that encodes N-terminal and internal fragments of various sizes of the kinase protein.

Several techniques are known in the art for screening gene products of combinatorial libraries made by point mutations or truncation and for screening cDNA libraries for gene products having a selected property. Such techniques are adaptable for rapid screening of the gene libraries generated by the combinatorial mutagenesis of kinase proteins. The most widely used techniques, which are amenable to high through-put analysis for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique that enhances the frequency of functional mutants in the libraries, can be used in combination with the screening assays to identify kinase variants (Arkin and Yourvan (1992) *Proc. Natl. Acad. Sci. USA*

89:7811–7815; Delgrave et al. (1993) *Protein Engineering* 6(3):327–331).

An isolated kinase polypeptide of the invention can be used as an immunogen to generate antibodies that bind kinase proteins using standard techniques for polyclonal and monoclonal antibody preparation. The full-length kinase protein can be used or, alternatively, the invention provides antigenic peptide fragments of the kinase protein for use as immunogens. The antigenic peptide of the kinase protein comprises at least 8, preferably 10, 15, 20, or 30 amino acid residues of the amino acid sequence shown in SEQ ID NO:2 and encompasses an epitope of the kinase protein such that an antibody raised against the peptide forms a specific immune complex with the kinase protein. Preferred epitopes encompassed by the antigenic peptide are regions of a kinase protein that are located on the surface of the protein, e.g., hydrophilic regions.

Accordingly, another aspect of the invention pertains to anti-kinase polyclonal and monoclonal antibodies that bind a kinase protein. Polyclonal anti-kinase antibodies can be prepared by immunizing a suitable subject (e.g., rabbit, goat, mouse, or other mammal) with a kinase immunogen. The anti-kinase antibody titer in the immunized subject can be monitored over time by standard techniques, such as with an enzyme linked immunosorbent assay (ELISA) using immobilized kinase protein. At an appropriate time after immunization, e.g., when the anti-kinase antibody titers are highest, antibody-producing cells can be obtained from the subject and used to prepare monoclonal antibodies by standard techniques, such as the hybridoma technique originally described by Kohler and Milstein (1975) *Nature* 256:495–497, the human B-cell hybridoma technique (Kozbor et al. (1983) *Immunol. Today* 4:72), the EBV-hybridoma technique (Cole et al. (1985) in *Monoclonal Antibodies and Cancer Therapy*, ed. Reisfeld and Sell (Alan R. Liss, Inc., New York, N.Y.), pp. 77–96) or trioma techniques. The technology for producing hybridomas is well known (see generally Coligan et al., eds. (1994) *Current Protocols in Immunology* (John Wiley & Sons, Inc., New York, N.Y.); Galfre et al. (1977) *Nature* 266:55052; Kenneth (1980) in *Monoclonal Antibodies: A New Dimension In Biological Analyses* (Plenum Publishing Corp., NY; and Lerner (1981) *Yale J. Biol. Med.*, 54:387–402).

Alternative to preparing monoclonal antibody-secreting hybridomas, a monoclonal anti-kinase antibody can be identified and isolated by screening a recombinant combinatorial immunoglobulin library (e.g., an antibody phage display library) with a kinase protein to thereby isolate immunoglobulin library members that bind the kinase protein. Kits for generating and screening phage display libraries are commercially available (e.g., the Pharmacia *Recombinant Phage Antibody System*, Catalog No. 27–9400–01; and the Stratagene *SurfZAP ∂ Phage Display Kit*, Catalog No. 240612). Additionally, examples of methods and reagents particularly amenable for use in generating and screening antibody display library can be found in, for example, U.S. Pat. No. 5,223,409; PCT Publication Nos. WO 92/18619; WO 91/17271; WO 92/20791; WO 92/15679; 93/01288; WO 92/01047; 92/09690; and 90/02809; Fuchs et al. (1991) *Bio/Technology* 9:1370–1372; Hay et al. (1992) *Hum. Antibod. Hybridomas* 3:81–85; Huse et al. (1989) *Science* 246:1275–1281; Griffiths et al (1993) *EMBO J*. 12:725–734.

Additionally, recombinant anti-kinase antibodies, such as chimeric and humanized monoclonal antibodies, comprising both human and nonhuman portions, which can be made using standard recombinant DNA techniques, are within the scope of the invention. Such chimeric and humanized monoclonal antibodies can be produced by recombinant DNA techniques known in the art, for example using methods described in PCT Publication Nos. WO 86101533 and WO 87/02671; European Patent Application Nos. 184,187, 171, 496, 125,023, and 173,494; U.S. Pat. Nos. 4,816,567 and 5,225,539; European Patent Application 125,023; Better et al. (1988) *Science* 240:1041–1043; Liu et al. (1987) *Proc. Natl. Acad. Sci. USA* 84:3439–3443; Liu et al. (1987) *J. Immunol*. 139:3521–3526; Sun et al. (1987) *Proc. Natl. Acad. Sci. USA* 84:214–218; Nishimura et al. (1987) *Canc. Res*. 47:999–1005; Wood et al. (1985) *Nature* 314:446–449; Shaw et al. (1988) *J. Natl. Cancer Inst*. 80:1553–1559); Morrison (1985) *Science* 229:1202–1207; Oi et al. (1986) *Bio/Techniques* 4:214; Jones et al. (1986) *Nature* 321:552–525; Verhoeyan et al. (1988) *Science* 239:1534; and Beidler et al. (1988) *J. Immunol*. 141:4053–4060.

Completely human antibodies are particularly desirable for therapeutic treatment of human patients. Such antibodies can be produced using transgenic mice that are incapable of expressing endogenous immunoglobulin heavy and light chains genes, but which can express human heavy and light chain genes. See, for example, Lonberg and Huszar (1995) *Int. Rev. Immunol*. 13:65–93); and U.S. Pat. Nos. 5,625,126; 5,633,425; 5,569,825; 5,661,016; and 5,545,806. In addition, companies such as Abgenix, Inc. (Freemont, Calif.), can be engaged to provide human antibodies directed against a selected antigen using technology similar to that described above.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. This technology is described by Jespers et al. (1994) *Bio/Technology* 12:899–903).

An anti-kinase antibody (e.g., monoclonal antibody) can be used to isolate kinase proteins by standard techniques, such as affinity chromatography or immunoprecipitation. An anti-kinase antibody can facilitate the purification of natural kinase protein from cells and of recombinantly produced kinase protein expressed in host cells. Moreover, an anti-kinase antibody can be used to detect kinase protein (e.g., in a cellular lysate or cell supernatant) in order to evaluate the abundance and pattern of expression of the kinase protein. Anti-kinase antibodies can be used diagnostically to monitor protein levels in tissue as part of a clinical testing procedure to, for example, determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

Further, an antibody (or fragment thereof) may be conjugated to a therapeutic moiety such as a cytotoxin, a therapeutic agent or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). The conjugates of the invention can be used for modifying a given biological response, the drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, .alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84:Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev., 62:119–58 (1982). Alternatively, an antibody can be conjugated to a second antibody to form an antibody heteroconjugate as described by Segal in U.S. Pat. No. 4,676,980.

III. Recombinant Expression Vectors and Host Cells

Another aspect of the invention pertains to vectors, preferably expression vectors, containing a nucleic acid encoding a kinase protein (or a portion thereof). "Vector" refers to a nucleic acid molecule capable of transporting another nucleic acid to which it has been linked, such as a "plasmid", a circular double-stranded DNA loop into which additional DNA segments can be ligated, or a viral vector, where additional DNA segments can be ligated into the viral genome. The vectors are useful for autonomous replication in a host cell or may be integrated into the genome of a host cell upon introduction into the host cell, and thereby are replicated along with the host genome (e.g., nonepisomal mammalian vectors). Expression vectors are capable of directing the expression of genes to which they are operably linked. In general, expression vectors of utility in recombinant DNA techniques are often in the form of plasmids (vectors). However, the invention is intended to include such other forms of expression vectors, such as viral vectors (e.g., replication-defective retroviruses, adenoviruses, and adeno-associated viruses), that serve equivalent functions.

The recombinant expression vectors of the invention comprise a nucleic acid of the invention in a form suitable for expression of the nucleic acid in a host cell. This means that the recombinant expression vectors include one or more regulatory sequences, selected on the basis of the host cells to be used for expression, operably linked to the nucleic acid sequence to be expressed. "Operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). See, for example, Goeddel (1990) in *Gene Expression Technology: Methods in Enzymology* 185 (Academic Press, San Diego, Calif.). Regulatory sequences include those that direct constitutive expression of a nucleotide sequence in many types of host cells and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or polypeptides, including fusion proteins or polypeptides, encoded by nucleic acids as described herein (e.g., kinase proteins, mutant forms of kinase proteins, fusion proteins, etc.). It is further recognized that the nucleic acid sequences of the invention can be altered to contain codons, which are preferred, or non-preferred, for a particular expression system. For example, the nucleic acid can be one in which at least one altered codon, and preferably at least 10%, or 20% of the codons have been altered such that the sequence is optimized for expression in *E. coli*, yeast, human, insect or CHO cells. Methods for determining codon usage are well known in the art.

The recombinant expression vectors of the invention can be designed for expression of kinase protein in prokarygtic or eukaryotic host cells. Expression of proteins in prokaryotes is most often carried out in *E. coli* with vectors containing constitutive or inducible promoters directing the expression of either fusion or nonfusion proteins. Fusion vectors add a number of amino acids to a protein encoded therein, usually to the amino terminus of the recombinant protein. Typical fusion expression vectors include pGEX (Pharmacia Biotech Inc; Smith and Johnson (1988) *Gene* 67:31–40), pMAL (New England Biolabs, Beverly, Mass.), and pRIT5 (Pharmacia, Piscataway, N.J.) which fuse glutathione S-transferase (GST), maltose E binding protein, or protein A, respectively, to the target recombinant protein. Examples of suitable inducible nonfusion *E. coli* expression vectors include pTrc (Amann et al. (1988) *Gene* 69:301–315) and pET 11d (Studier et al. (1990) in *Gene Expression Technology: Methods in Enzymology* 185

(Academic Press, San Diego, Calif.), pp. 60–89). Strategies to maximize recombinant protein expression in E. coli can be found in Gottesman (1990) in *Gene Expression Technology: Methods in Enzymology* 185 (Academic Press, Calif.), pp. 119–128 and Wada et al. (1992) *Nucleic Acids Res.* 20:2111–2118. Target gene expression from the pTrc vector relies on host RNA polymerase transcription from a hybrid trp-lac fusion promoter.

Suitable eukaryotic host cells include insect cells (examples of Baculovirus vectors available for expression of proteins in cultured insect cells (e.g., Sf 9 cells) include the pAc series (Smith et al. (1983) *Mol. Cell Biol.* 3:2156–2165) and the pVL series (Lucklow and Summers (1989) *Virology* 170:31–39)); yeast cells (examples of vectors for expression in yeast *S. cerevisiae* include pYepSec1 (Baldari et al. (1987) *EMBO J.* 6:229–234), pMFa (Kurjan and Herskowitz (1982) *Cell* 30:933–943), pJRY88 (Schultz et al. (1987) *Gene* 54:113–123), pYES2 (Invitrogen Corporation, San Diego, Calif.), and pPicZ (Invitrogen Corporation, San Diego, Calif.)); or mammalian cells (mammalian expression vectors include pCDM8 (Seed (1987) *Nature* 329:840) and pMT2PC (Kaufmnan et al. (1987) *EMBO J.* 6:187:195)). Suitable mammalian cells include Chinese hamster ovary cells (CHO) or COS cells. In mammalian cells, the expression vector's control functions are often provided by viral regulatory elements. For example, commonly used promoters are derived from polyoma, Adenovirus 2, cytomegalovirus, and Simian Virus 40. For other suitable expression systems for both prokaryotic and eukaryotic cells, see chapters 16 and 17 of Sambrook et al. (1989) *Molecular Cloning: A Laboratory Manual* (2d ed., Cold Spring Harbor Laboratory Press, Plainview, N.Y.). See, Goeddel (1990) in *Gene Expression Technology: Methods in Enzymology* 185 (Academic Press, San Diego, Calif.). Alternatively, the recombinant expression vector can be transcribed and translated in vitro, for example using T7 promoter regulatory sequences and T7 polymerase.

The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell but are still included within the scope of the term as used herein. A "purified preparation of cells", as used herein, refers to, in the case of plant or animal cells, an in vitro preparation of cells and not an entire intact plant or animal. In the case of cultured cells or microbial cells, it consists of a preparation of at least 10% and more preferably 50% of the subject cells.

In one embodiment, the expression vector is a recombinant mammalian expression vector that comprises tissue-specific regulatory elements that direct expression of the nucleic acid preferentially in a particular cell type. Suitable tissue-specific promoters include the albumin promoter (liver-specific; Pinkert et al. (1987) *Genes Dev.* 1:268–277), lymphoid-specific promoters (Calame and Eaton (1988) *Adv. Immunol.* 43:235–275), particular promoters of T-cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Patent Publication No. 264, 166). Developmentally-regulated promoters are also encompassed, for example the murine hox promoters (Kessel and Gruss (1990) *Science* 249:374–379), the α-fetoprotein promoter (Campes and Tilghman (1989) *Genes Dev.* 3:537–546), and the like.

The invention further provides a recombinant expression vector comprising a DNA molecule of the invention cloned into the expression vector in an antisense orientation. That is, the DNA molecule is operably linked to a regulatory sequence in a manner that allows for expression (by transcription of the DNA molecule) of an RNA molecule that is antisense to kinase mRNA. Regulatory sequences operably linked to a nucleic acid cloned in the antisense orientation can be chosen to direct the continuous expression of the antisense RNA molecule in a variety of cell types, for instance viral promoters and/or enhancers, or regulatory sequences can be chosen to direct constitutive, tissue-specific, or cell-type-specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes see Weintraub et al. (1986) Reviews—Trends in Genetics, Vol. 1(1).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (1989) *Molecular Cloning: A Laboraty Manual* (2d ed., Cold Spring Harbor Laboratory Press, Plainview, N.Y.) and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin, and methotrexate. Nucleic acid encoding a selectable marker can be introduced into a host cell on the same vector as that encoding a kinase protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) kinase protein. Accordingly, the invention further provides methods for producing kinase protein using the host cells of the invention. In one embodiment, the method comprises culturing the host cell of the invention, into which a recombinant expression vector encoding a kinase protein has been introduced, in a suitable medium such that kinase protein is produced. In another embodiment, the method further comprises isolating kinase protein from the medium or the host cell.

The host cells of the invention can also be used to produce nonhuman transgenic animals. For example, in one embodiment, a host cell of the invention is a fertilized oocyte or an embryonic stem cell into which a kinase-coding sequence has been introduced. Such host cells can then be used to create nonhuman transgenic animals in which exogenous kinase sequences have been introduced into their genome or homologous recombinant animals in which endogenous kinase sequences have been altered. Such animals are useful for studying the function and/or activity of kinase genes and proteins and for identifying and/or evaluating modulators of kinase activity. As used herein, a "transgenic animal" is a nonhuman animal, preferably a mammal, more preferably a rodent such as a rat or mouse, in which one or more of the cells of the animal includes a transgene. Other examples of transgenic animals include nonhuman primates, sheep, dogs, cows, goats, chickens, amphibians, etc. A transgene is exogenous DNA that is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a nonhuman animal, preferably a mammal, more preferably a mouse, in which an endogenous kinase gene has been altered by homologous recombination between the endogenous gene and an exogenous DNA molecule introduced into a cell of the animal, e.g., an embryonic cell of the animal, prior to development of the animal.

A transgenic animal of the invention can be created by introducing kinase-encoding nucleic acid into the male pronuclei of a fertilized oocyte, e.g., by microinjection, retroviral infection, and allowing the oocyte to develop in a pseudopregnant female foster animal. The kinase cDNA sequence can be introduced as a transgene into the genome of a nonhuman animal. Alternatively, a homolog of the kinase gene can be isolated based on hybridization and used as a transgene. Intronic sequences and polyadenylation signals can also be included in the transgene to increase the efficiency of expression of the transgene. A tissue-specific regulatory sequence(s) can be operably linked to the kinase transgene to direct expression of kinase protein to particular cells. Methods for generating transgenic animals via embryo manipulation and microinjection, particularly animals such as mice, have become conventional in the art and are described, for example, in U.S. Pat. Nos. 4,736,866, 4,870,009, and 4,873,191 and in Hogan (1986) *Manipulating the Mouse Embryo* (Cold Spring Harbor Laboratory Press, Cold Spring Harbor, N.Y., 1986). Similar methods are used for production of other transgenic animals. A transgenic founder animal can be identified based upon the presence of the kinase transgene in its genome and/or expression of kinase mRNA in tissues or cells of the animals. A transgenic founder animal can then be used to breed additional animals carrying the transgene. Moreover, transgenic animals carrying a transgene encoding kinase gene can further be bred to other transgenic animals carrying other transgenes.

To create a homologous recombinant animal, one prepares a vector containing at least a portion of a kinase gene or a homolog of the gene into which a deletion, addition, or substitution has been introduced to thereby alter, e.g., functionally disrupt, the kinase gene. In a preferred embodiment, the vector is designed such that, upon homologous recombination, the endogenous kinase gene is functionally disrupted (i.e., no longer encodes a functional protein; such vectors are also referred to as "knock out" vectors). Alternatively, the vector can be designed such that, upon homologous recombination, the endogenous kinase gene is mutated or otherwise altered but still encodes functional protein (e.g., the upstream regulatory region can be altered to thereby alter the expression of the endogenous kinase protein). In the homologous recombination vector, the altered portion of the kinase gene is flanked at its 5N and 3N ends by additional nucleic acid of the kinase gene to allow for homologous recombination to occur between the exogenous kinase gene carried by the vector and an endogenous kinase gene in an embryonic stem cell. The additional flanking kinase nucleic acid is of sufficient length for successful homologous recombination with the endogenous gene. Typically, several kilobases of flanking DNA (both at the 5' and 3' ends) are included in the vector (see, e.g., Thomas and Capecchi (1987) *Cell* 51:503 for a description of homologous recombination vectors). The vector is introduced into an embryonic stem cell line (e.g., by electroporation), and cells in which the introduced kinase gene has homologously recombined with the endogenous kinase gene are selected (see, e.g., Li et al. (1992) *Cell* 69:915). The selected cells are then injected into a blastocyst of an animal (e.g., a mouse) to form aggregation chimeras (see, e.g., Bradley (1987) in *Teratocarcinomas and Embryonic Stem Cells: A Practical Approach*, ed. Robertson (IRL, Oxford), pp. 113–152). A chimeric embryo can then be implanted into a suitable pseudopregnant female foster animal and the embryo brought to term. Progeny harboring the homologously-recombined DNA in their germ cells can be used to breed animals in which all cells of the animal contain the homologously recombined DNA by germline transmission of the transgene. Methods for constructing homologous recombination vectors and homologous recombinant animals are described further in Bradley (1991) *Current Opinion in Bio/Technology* 2:823–829 and in PCT Publication Nos. WO 90/11354, WO 91/01140, WO 92/0968, and WO 93/04169.

In another embodiment, transgenic nonhuman animals containing selected systems that allow for regulated expression of the transgene can be produced. One example of such a system is the cre/loxP recombinase system of bacteriophage P1. For a description of the cre/loxP recombinase system, see, e.g., Lakso et al. (1992) *Proc. Natl. Acad. Sci. USA* 89:6232–6236. Another example of a recombinase system is the FLP recombinase system of *Saccharomyces cerevisiae* (O'Gorman et al. (1991) *Science* 251:1351–1355). If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the nonhuman transgenic animals described herein can also be produced according to the methods described in Wilmut et al. (1997) *Nature* 385:810–813 and PCT Publication Nos. WO 97/07668 and WO 97/07669.

IV. Pharmaceutical Compositions

The kinase nucleic acid molecules, kinase proteins, and anti-kinase antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The compositions of the invention are useful to treat any of the disorders discussed herein. The compositions are provided in therapeutically effective amounts. By "therapeutically effective amounts" is intended an amount sufficient to modulate the desired response. As defined herein, a therapeutically effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or, preferably, can include a series of treatments. In a preferred example, a subject is treated with antibody, protein, or polypeptide in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of antibody, protein, or polypeptide used for treatment may increase or decrease over the course of a particular treatment. Changes in dosage may result and become apparent from the results of diagnostic assays as described herein.

The present invention encompasses agents which modulate expression or activity. An agent may, for example, be a small molecule. For example, such small molecules include, but are not limited to, peptides, peptidomimetics, amino acids, amino acid analogs, polynucleotides, polynucleotide analogs, nucleotides, nucleotide analogs, organic or inorganic compounds (i.e.,. including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a small molecule depend upon the potency of the small molecule with respect to the expression or activity to be modulated. Such appropriate doses may be determined using the assays described herein. When one or more of these small molecules is to be administered to an animal (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes, or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL∂ (BASF; Parsippany, N.J.), or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride, in the composition. Prolonged absorption of the injectable compositions can be brought about by including in the composition an agent that delays absorption, for example, aluminum monostearate and gelatin.

Sterile injectable solutions can be prepared by incorporating the active compound (e.g., a kinase protein or anti-kinase antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying, which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth, or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds are delivered in the form of an aerosol spray from a pressurized container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated with each unit containing a predetermined quantity of active compound calculated to produce the desired therapeutic effect in association with the required pharmaceutical carrier. Depending on the type and severity of the disease, about 1 $\mu$g/kg to about 15 mg/kg (e.g., 0.1 to 20 mg/kg) of antibody is an initial candidate dosage for administration to the patient, whether, for example, by one or more separate administrations, or by continuous infusion. A typical daily dosage might range from about 1 $\mu$g/kg to about 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays. An exemplary dosing regimen is disclosed in WO 94/04188. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (U.S. Pat. No. 5,328,470), or by stereotactic injection (see, e.g., Chen et al. (1994) *Proc. Natl. Acad. Sci. USA* 91:3054–3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologs, and antibodies described herein can be used in one or more of the following methods: (a) screening assays; (b) detection assays (e.g., chromosomal mapping, tissue typing, forensic biology); (c) predictive medicine (e.g., diagnostic assays, prognostic assays, monitoring clinical trials, and pharmacogenomics); and (d) methods of treatment (e.g., therapeutic and prophylactic). The isolated nucleic acid molecules of the invention can be used to express kinase protein (e.g., via a recombinant expression vector in a host cell in gene therapy applications), to detect kinase mRNA (e.g., in a biological sample) or a genetic lesion in a kinase gene, and to modulate kinase activity. In addition, the kinase proteins can be used to screen drugs or compounds that modulate cellular growth and/or metabolism as well as to treat disorders characterized by insufficient or excessive production of kinase protein or production of kinase protein forms that have decreased or aberrant activity compared to kinase wild type protein. In addition, the anti-kinase antibodies of the invention can be used to detect and isolate kinase proteins and modulate kinase activity.

A. Screening Assays

The invention provides a method (also referred to herein as a "screening assay") for identifying modulators, i.e., candidate or test compounds or agents (e.g., peptides, peptidomimetics, small molecules, or other drugs) that bind to kinase proteins or have a stimulatory or inhibitory effect on, for example, kinase expression or kinase activity.

The test compounds of the present invention can be obtained using any of the numerous approaches in combinatorial library methods known in the art, including biological libraries, spatially-addressable parallel solid phase or solution phase libraries, synthetic library methods requiring deconvolution, the "one-bead one-compound" library method, and synthetic library methods using affinity chromatography selection. The biological library approach is limited to peptide libraries, while the other four approaches are applicable to peptide, nonpeptide oligomer, or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. USA* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (I994) *J. Med. Chem.* 37:1233.

Libraries of compounds may be presented in solution (e.g., Houghten (1992) *Bio/Techniques* 13:412–421), or on beads (Lam (1991) *Nature* 354:82–84), chips (Fodor (1993) *Nature* 364:555–556), bacteria (U.S. Pat. No. 5,223,409), spores (U.S. Pat. Nos. 5,571,698; 5,403,484; and 5,223,409), plasmids (Cull et al. (1992) *Proc. Natl. Acad. Sci. USA* 89:1865–1869), or phage (Scott and Smith (1990) *Science* 249:386–390; Devlin (1990) *Science* 249:404–406; Cwirla et al. (1990) *Proc. Natl. Acad. Sci. USA* 87:6378–6382; and Felici (1991) *J. Mol. Biol.* 222:301–310).

Determining the ability of the test compound to bind to the kinase protein can be accomplished, for example, by coupling the test compound with a radioisotope or enzymatic label such that binding of the test compound to the kinase protein or biologically active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product.

In a similar manner, one may determine the ability of the kinase protein to bind to or interact with a kinase target molecule. By "target molecule" is intended a molecule with which a kinase protein binds or interacts in nature. In a preferred embodiment, the ability of the kinase protein to bind to or interact with a kinase target molecule can be determined by monitoring the activity of the target molecule. For example, the activity of the target molecule can be monitored by detecting induction of a cellular second messenger of the target (e.g., intracellular $Ca^{2+}$, diacylglycerol, IP3, etc.), detecting catalytic/enzymatic activity of the target on an appropriate substrate, detecting the induction of a reporter gene (e.g., a kinase-responsive regulatory element operably linked to a nucleic acid encoding a detectable marker, e.g., luciferase), or detecting a cellular response, for example, cellular differentiation or cell proliferation. Biochemical events, substrates, and effector molecules, include, but are not limited to, those discussed above with reference to the functions shown in FIG. 4, ankyrin related functions, and RIP, RIP-like, and CARDIAK-like functions.

In yet another embodiment, an assay of the present invention is a cell-free assay comprising contacting a kinase protein or biologically active portion thereof with a test compound and determining the ability of the test compound to bind to the kinase protein or biologically active portion thereof Binding of the test compound to the kinase protein can be determined either directly or indirectly as described above. In a preferred embodiment, the assay includes contacting the kinase protein or biologically active portion thereof with a known compound that binds kinase protein to form an assay mixture, contacting the assay mixture with a test compound, and determining the ability of the test compound to preferentially bind to kinase protein or biologically active portion thereof as compared to the known compound.

In another embodiment, an assay is a cell-free assay comprising contacting kinase protein or biologically active portion thereof with a test compound and determining the ability of the test compound to modulate (e.g., stimulate or inhibit) the activity of the kinase protein or biologically active portion thereof. Determining the ability of the test compound to modulate the activity of a kinase protein can be accomplished, for example, by determining the ability of the kinase protein to bind to a kinase target molecule as described above for determining direct binding. In an alternative embodiment, determining the ability of the test compound to modulate the activity of a kinase protein can be accomplished by determining the ability of the kinase protein to further modulate a kinase target molecule. For example, the catalytic/enzymatic activity of the target molecule on an appropriate substrate can be determined as previously described.

In yet another embodiment, the cell-free assay comprises contacting the kinase protein or biologically active portion thereof with a known compound that binds a kinase protein to form an assay mixture, contacting the assay mixture with a test compound, and determining the ability of the test compound to preferentially bind to or modulate the activity of a kinase target molecule.

In the above-mentioned assays, it may be desirable to immobilize either a kinase protein or its target molecule to facilitate separation of complexed from uncomplexed forms of one or both of the proteins, as well as to accommodate automation of the assay. In one embodiment, a fusion protein can be provided that adds a domain that allows one or both of the proteins to be bound to a matrix. For example, glutathione-S-transferase/kinase fusion proteins or glutathione-S-transferase/target fusion proteins can be adsorbed onto glutathione sepharose beads (Sigma Chemical, St. Louis, Mo.) or glutathione-derivatized microtitre plates, which are then combined with the test compound or the test compound and either the nonadsorbed target protein or kinase protein, and the mixture incubated under conditions conducive to complex formation (e.g., at physiological conditions for salt and pH). Following incubation, the beads or microtitre plate wells are washed to remove any unbound components and complex formation is measured either directly or indirectly, for example, as described above. Alternatively, the complexes can be dissociated from the matrix, and the level of kinase binding or activity determined using standard techniques.

Other techniques for immobilizing proteins on matrices can also be used in the screening assays of the invention. For example, either kinase protein or its target molecule can be immobilized utilizing conjugation of biotin and streptavidin. Biotinylated kinase molecules or target molecules can be prepared from biotin-NHS (N-hydroxy-succinimide) using techniques well known in the art (e.g., biotinylation kit, Pierce Chemicals, Rockford, Ill.), and immobilized in the wells of streptavidin-coated 96-well plates (Pierce Chemicals). Alternatively, antibodies reactive with a kinase protein or target molecules but which do not interfere with binding of the kinase protein to its target molecule can be derivatized to the wells of the plate, and unbound target or kinase protein trapped in the wells by antibody conjugation. Methods for detecting such complexes, in addition to those described above for the GST-immobilized complexes, include immunodetection of complexes using antibodies reactive with the kinase protein or target molecule, as well as enzyme-linked assays that rely on detecting an enzymatic activity associated with the kinase protein or target molecule.

In another embodiment, modulators of kinase expression are identified in a method in which a cell is contacted with a candidate compound and the expression of kinase mRNA or protein in the cell is determined relative to expression of kinase mRNA or protein in a cell in the absence of the candidate compound. When expression is greater (statistically significantly greater) in the presence of the candidate compound than in its absence, the candidate compound is identified as a stimulator of kinase mRNA or protein expression. Alternatively, when expression is less (statistically significantly less) in the presence of the candidate compound than in its absence, the candidate compound is identified as an inhibitor of kinase mRNA or protein expression. The level of kinase mRNA or protein expression in the cells can be determined by methods described herein for detecting kinase mRNA or protein.

In yet another aspect of the invention, the kinase proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Bio/Techniques 14:920–924; Iwabuchi et al. (1993) Oncogene 8:1693–1696; and PCT Publication No. WO 94/10300), to identify other proteins, which bind to or interact with kinase protein ("kinase-binding proteins" or "kinase-bp") and modulate kinase activity. Such kinase-binding proteins are also likely to be involved in the propagation of signals by the kinase proteins as, for example, upstream or downstream elements of a signaling pathway.

This invention further pertains to novel agents identified by the above-described screening assays and uses thereof for treatments as described herein.

B. Detection Assays

Portions or fragments of the cDNA sequences identified herein (and the corresponding complete gene sequences) can be used in numerous ways as polynucleotide reagents. For example, these sequences can be used to: (1) map their respective genes on a chromosome; (2) identify an individual from a minute biological sample (tissue typing); and (3) aid in forensic identification of a biological sample. These applications are described in the subsections below.

1. Chromosome Mapping

The isolated complete or partial kinase gene sequences of the invention can be used to map their respective kinase genes on a chromosome, thereby facilitating the location of gene regions associated with genetic disease. Computer analysis of kinase sequences can be used to rapidly select PCR primers (preferably 15–25 bp in length) that do not span more than one exon in the genomic DNA, thereby simplifying the amplification process. These primers can then be used for PCR screening of somatic cell hybrids containing individual human chromosomes. Only those hybrids containing the human gene corresponding to the kinase sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow (because they lack a particular enzyme), but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes (D'Eustachio et al. (1983) Science 220:919–924). Somatic cell hybrids containing only fragments of human chromosomes can also be produced by using human chromosomes with translocations and deletions.

Other mapping strategies that can similarly be used to map a kinase sequence to its chromosome include in situ hybridization (described in Fan et al. (1990) Proc. Natl. Acad. Sci. USA 87:6223–27), pre-screening with labeled flow-sorted chromosomes, and pre-selection by hybridization to chromosome specific cDNA libraries. Furthermore, fluorescence in situ hybridization (FISH) of a DNA sequence to a metaphase chromosomal spread can be used to provide a precise chromosomal location in one step. For a review of this technique, see Verma et al. (1988) Human Chromosomes. A Manual of Basic Techniques (Pergamon Press, NY). The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results in a reasonable amount of time.

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between genes and disease, mapped to the same chromosomal region, can then be identified through linkage analysis (co-inheritance of physically adjacent genes), described in, e.g., Egeland et al. (1987) Nature 325:783–787.

Moreover, differences in the DNA sequences between individuals affected and unaffected with a disease associated with the kinase gene can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The kinase sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes and probed on a Southern blot to yield unique bands for identification. The sequences of the present invention are useful as additional DNA markers for RFLP (described in U.S. Pat. No. 5,272,057).

Furthermore, the sequences of the present invention can be used to provide an alternative technique for determining the actual base-by-base DNA sequence of selected portions of an individual's genome. Thus, the kinase sequences of the invention can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The kinase sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. The noncoding sequence of SEQ ID NO:1 can comfortably provide positive individual identification with a panel of perhaps 10 to 1,000 primers that each yield a noncoding amplified sequence of 100 bases. If predicted coding sequences, such as in SEQ ID NO:1 are used, a more appropriate number of primers for positive individual identification would be 500 to 2,000.

3. Use of Partial Kinase Sequences in Forensic Biology

DNA-based identification techniques can also be used in forensic biology. In this manner, PCR technology can be used to amplify DNA sequences taken from very small biological samples such as tissues, e.g., hair, skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" that is unique to a particular individual. As mentioned above, actual base sequence information can be used for identification as an accurate alternative to patterns formed by restriction enzyme generated fragments. Sequences targeted to the noncoding region of SEQ ID NO:1 are particularly appropriate for this use as greater numbers of polymorphisms occur in the noncoding region, making it easier to differentiate individuals using this technique. Examples of polynucleotide reagents include the kinase sequence or portions thereof, e.g., fragments derived from the noncoding region of SEQ ID NO:1 having a length of at least 20 or 30 bases.

The kinase sequences described herein can further be used to provide polynucleotide reagents, e.g., labeled or labelable probes that can be used in, for example, an in situ hybridization technique, to identify a specific tissue. This can be very useful in cases where a forensic pathologist is presented with a tissue of unknown origin. Panels of such kinase probes, can be used to identify tissue by species and/or by organ type.

In a similar fashion, these reagents, e.g., kinase primers or probes can be used to screen tissue culture for contamination (i.e., screen for the presence of a mixture of different types of cells in a culture).

C. Predictive Medicine

The present invention also pertains to the field of predictive medicine in which diagnostic assays, prognostic assays, pharmacogenomics, and monitoring clinical trails are used for prognostic (predictive) purposes to thereby treat an individual prophylactically. These applications are described in the subsections below.

1. Diagnostic Assays

One aspect of the present invention relates to diagnostic assays for detecting kinase protein and/or nucleic acid expression as well as kinase activity, in the context of a biological sample. An exemplary method for detecting the presence or absence of kinase proteins in a biological sample involves obtaining a biological sample from a test subject and contacting the biological sample with a compound or an agent capable of detecting kinase protein or nucleic acid (e.g., mRNA, genomic DNA) that encodes kinase protein such that the presence of kinase protein is detected in the biological sample. Results obtained with a biological sample from the test subject may be compared to results obtained with a biological sample from a control subject.

"Misexpression or aberrant expression", as used herein, refers to a non-wild type pattern of gene expression, at the RNA or protein level. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild type in terms of decreased expression (as compared with wild type) in a predetermined cell type or tissue type; a pattern of expression that differs from wild type in terms of the splicing size, amino acid sequence, post-transitional modification, or biological activity of the expressed polypeptide; a pattern of expression that differs from wild type in terms of the effect of an environmental stimulus or extracellular stimulus on expression of the gene, e.g., a pattern of increased or decreased expression (as compared with wild type) in the presence of an increase or decrease in the strength of the stimulus.

A preferred agent for detecting kinase mRNA or genomic DNA is a labeled nucleic acid probe capable of hybridizing to kinase mRNA or genomic DNA. The nucleic acid probe can be, for example, a full-length or partial kinase nucleic acid, such as the nucleic acid of SEQ ID NO:1, or a portion thereof, such as a nucleic acid molecule of at least 15, 30, 50, 100, 250, or 500 nucleotides in length and sufficient to specifically hybridize under stringent conditions to kinase mRNA or genomic DNA. Other suitable probes for use in the diagnostic assays of the invention are described herein.

A preferred agent for detecting kinase protein is an antibody capable of binding to kinase protein, preferably an antibody with a detectable label. Antibodies can be polyclonal, or more preferably, monoclonal. An intact antibody, or a fragment thereof (e.g., Fab or F(abN)$_2$ )can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

The term "biological sample" is intended to include tissues, cells, and biological fluids isolated from a subject, as well as tissues, cells, and fluids present within a subject. That is, the detection method of the invention can be used to detect kinase mRNA, protein, or genomic DNA in a biological sample in vitro as well as in vivo. For example, in vitro techniques for detection of kinase mRNA include Northern hybridizations and in situ hybridizations. In vitro techniques for detection of kinase protein include enzyme linked immunosorbent assays (ELISAs), Western blots, immunoprecipitations, and immunofluorescence. In vitro techniques for detection of kinase genomic DNA include Southern hybridizations. Furthermore, in vivo techniques for detection of kinase protein include introducing into a subject a labeled anti-kinase antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. Biological samples may be obtained from blood, serum, cells, or tissue of a subject.

The invention also encompasses kits for detecting the presence of kinase proteins in a biological sample (a test sample). Such kits can be used to determine if a subject is suffering from or is at increased risk of developing a disorder associated with aberrant expression of kinase protein. For example, the kit can comprise a labeled compound or agent capable of detecting kinase protein or mRNA in a biological sample and means for determining the amount of a kinase protein in the sample (e.g., an anti-kinase antibody or an oligonucleotide probe that binds to DNA encoding the kinase protein, e.g., SEQ ID NO:2). Kits can also include instructions for observing that the tested subject is suffering from or is at risk of developing a disorder associated with aberrant expression of kinase sequences if the amount of kinase protein or mRNA is above or below a normal level.

For antibody-based kits, the kit can comprise, for example: (1) a first antibody (e.g., attached to a solid support) that binds to kinase protein; and, optionally, (2) a second, different antibody that binds to kinase protein or the first antibody and is conjugated to a detectable agent. For oligonucleotide-based kits, the kit can comprise, for example: (1) an oligonucleotide, e.g., a detectably labeled oligonucleotide, that hybridizes to a kinase nucleic acid sequence or (2) a pair of primers useful for amplifying a kinase nucleic acid molecule.

The kit can also comprise, e.g., a buffering agent, a preservative, or a protein stabilizing agent. The kit can also comprise components necessary for detecting the detectable agent (e.g., an enzyme or a substrate). The kit can also contain a control sample or a series of control samples that can be assayed and compared to the test sample contained. Each component of the kit is usually enclosed within an individual container, and all of the various containers are within a single package along with instructions for observing whether the tested subject is suffering from or is at risk of developing a disorder associated with aberrant expression of kinase proteins.

2. Prognostic Assays

The methods described herein can furthermore be utilized as diagnostic or prognostic assays to identify subjects having or at risk of developing a disease or disorder associated with kinase protein, kinase nucleic acid expression, or kinase activity. Prognostic assays can be used for prognostic or predictive purposes to thereby prophylactically treat an individual prior to the onset of a disorder characterized by or associated with kinase protein, kinase nucleic acid expression, or kinase activity.

Thus, the present invention provides a method in which a test sample is obtained from a subject, and kinase protein or nucleic acid (e.g., mRNA, genomic DNA) is detected, wherein the presence of kinase protein or nucleic acid is diagnostic for a subject having or at risk of developing a disease or disorder associated with aberrant kinase expression or activity. As used herein, a "test sample" refers to a biological sample obtained from a subject of interest. For example, a test sample can be a biological fluid cell sample, or tissue.

Furthermore, using the prognostic assays described herein, the present invention provides methods for determining whether a subject can be administered a specific agent (e.g., an agonist, antagonist, peptidomimetic, protein, peptide, nucleic acid, small molecule, or other drug candidate) or class of agents (e.g., agents of a type that decrease kinase activity) to effectively treat a disease or disorder associated with aberrant kinase expression or activity. In this manner, a test sample is obtained and kinase protein or nucleic acid is detected. The presence of kinase protein or nucleic acid is diagnostic for a subject that can be administered the agent to treat a disorder associated with aberrant kinase expression or activity.

The methods of the invention can also be used to detect genetic lesions or mutations in a kinase gene, thereby determining if a subject with the lesioned gene is at risk for a disorder characterized by aberrant cell proliferation and/or differentiation. In preferred embodiments, the methods include detecting, in a sample of cells from the subject, the presence or absence of a genetic lesion or mutation characterized by at least one of an alteration affecting the integrity of a gene encoding a kinase-protein, or the misexpression of the kinase gene. For example, such genetic lesions or mutations can be detected by ascertaining the existence of at least one of: (1) a deletion of one or more nucleotides from a kinase gene; (2) an addition of one or more nucleotides to a kinase gene; (3) a substitution of one or more nucleotides of a kinase gene; (4) a chromosomal rearrangement of a kinase gene; (5) an alteration in the level of a messenger RNA transcript of a kinase gene; (6) an aberrant modification of a kinase gene, such as of the methylation pattern of the genomic DNA; (7) the presence of a non-wild-type splicing pattern of a messenger RNA transcript of a kinase gene; (8) a non-wild-type level of a kinase-protein; (9) an allelic loss of a kinase gene; and (10) an inappropriate post-translational modification of a kinase-protein. As described herein, there are a large number of assay techniques known in the art that can be used for detecting lesions in a kinase gene. Any cell type or tissue in which kinase proteins are expressed may be utilized in the prognostic assays described herein.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077–1080; and Nakazawa et al. (1994) *Proc. Natl. Acad. Sci. USA* 91:360–364), the latter of which can be particularly useful for detecting point mutations in the kinase-gene (see, e.g., Abravaya et al. (1995) *Nucleic Acids Res.* 23:675–682). It is anticipated that PCR and/or LCR may be desirable to use as a preliminary amplification step in conjunction with any of the techniques used for detecting mutations described herein.

Alternative amplification methods include self sustained sequence replication (Guatelli et al. (1990) *Proc. Natl. Acad. Sci. USA* 87:1874–1878), transcriptional amplification system (Kwoh et al. (1989) *Proc. Natl. Acad. Sci. USA* 86:1173–1177), Q-Beta Replicase (Lizardi et al. (1988) *Bio/Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a kinase gene from a sample cell can be identified by alterations in restriction enzyme cleavage patterns of isolated test sample and control DNA digested with one or more restriction endonucleases. Moreover, the use of sequence specific ribozymes (see, e.g., U.S. Pat. No. 5,498,531) can be used to score for the presence of specific mutations by development or loss of a ribozyme cleavage site.

In other embodiments, genetic mutations in a kinase molecule can be identified by hybridizing a sample and control nucleic acids, e.g., DNA or RNA, to high density arrays containing hundreds or thousands of oligonucleotides probes (Cronin et al. (1996) *Human Mutation* 7:244–255; Kozal et al. (1996) *Nature Medicine* 2:753–759). In yet another embodiment, any of a variety of sequencing reactions known in the art can be used to directly sequence the kinase gene and detect mutations by comparing the sequence of the sample kinase gene with the corresponding wild-type (control) sequence. Examples of sequencing reactions include those based on techniques developed by Maxim and Gilbert ((1977) *Proc. Natl. Acad. Sci. USA* 74:560) or Sanger.((1977) *Proc. Natl. Acad. Sci. USA* 74:5463). It is also contemplated that any of a variety of automated sequencing procedures can be utilized when performing the diagnostic assays ((1995) *Bio/Techniques* 19:448), including sequencing by mass spectrometry (see, e.g., PCT Publication No. WO 94/16101; Cohen et al. (1996) *Adv. Chromatogr.* 36:127–162; and Griffin et al. (1993) *Appl. Biochem. Biotechnol.* 38:147–159).

Other methods for detecting mutations in the kinase gene include methods in which protection from cleavage agents is used to detect mismatched bases in RNA/RNA or RNA/DNA heteroduplexes (Myers et al. (1985) *Science* 230:1242). See, also Cotton et al. (1988) *Proc. Natl. Acad. Sci. USA* 85:4397; Saleeba et al.,(1992) *Methods Enzymol.* 217:286–295. In a preferred embodiment, the control DNA or RNA can be labeled for detection.

In still another embodiment, the mismatch cleavage reaction employs one or more "DNA mismatch repair" enzymes that recognize mismatched base pairs in double-stranded DNA in defined systems for detecting and mapping point mutations in kinase cDNAs obtained from samples of cells. See, e.g., Hsu et al. (1994) *Carcinogenesis* 15:1657–1662.

According to an exemplary embodiment, a probe based on a kinase sequence, e.g., a wild-type kinase sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in kinase genes. For example, single-strand conformation polymorphism (SSCP) may be used to detect differences in electrophoretic mobility between mutant and wild-type nucleic acids (Orita et al. (1989) *Proc. Natl. Acad. Sci. USA* 86:2766; see also Cotton (1993) *Mutat. Res.* 285:125–144; Hayashi (1992) *Genet. Anal. Tech. Appl.* 9:73–79). The sensitivity of the assay may be enhanced by using RNA (rather than DNA), in which the secondary structure is more sensitive to a change in sequence. In a preferred embodiment, the subject method utilizes heteroduplex analysis to separate double-stranded heteroduplex molecules on the basis of changes in electrophoretic mobility (Keen et al. (1991) *Trends Genet.* 7:5).

In yet another embodiment, the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found (Saiki et al. (1986) *Nature* 324:163); Saiki et al. (1989) *Proc. Natl. Acad. Sci. USA* 86:6230). Such allele-specific oligonucleotides are hybridized to PCR-amplified target DNA or a number of different mutations when the oligonucleotides are attached to the hybridizing membrane and hybridized with labeled target DNA.

Alternatively, allele-specific amplification technology, which depends on selective PCR amplification, may be used in conjunction with the instant invention. Oligonucleotides used as primers for specific amplification may carry the mutation of interest in the center of the molecule so that amplification depends on differential hybridization (Gibbs et al. (1989) *Nucleic Acids Res.* 17:2437–2448) or at the extreme 3' end of one primer where, under appropriate conditions, mismatch can prevent or reduce polymerase extension (Prossner (1993) *Tibtech* 11:238). In addition, it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci. USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by utilizing prepackaged diagnostic kits comprising at least one probe nucleic acid or antibody reagent described herein, which may be conveniently used, e.g., in clinical settings to diagnose patients exhibiting symptoms or family history of a disease or illness involving a kinase gene.

3. Pharmacogenomics

Agents or modulators that have a stimulatory or inhibitory effect on kinase activity (e.g., kinase gene expression) as identified by a screening assay described herein, can be administered to individuals to treat (prophylactically or therapeutically) disorders associated with aberrant kinase activity as well as to modulate the cellular growth, differentiation and/or metabolism. In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharniacologically active drug. Thus, the pharmacogenomics of the individual permits the selection of effective agents (e.g., drugs) for prophylactic or therapeutic treatments based on a consideration of the individual's genotype. Such pharmacogenomics can further be used to determine appropriate dosages and therapeutic regimens. Accordingly, the activity of kinase protein, expression of kinase nucleic acid, or mutation content of kinase genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See, e.g., Linder (1997) *Clin. Chem.* 43(2):254–266. In general, two types of pharmacogenetic conditions can be differentiated. Genetic conditions transmitted as a single factor altering the way drugs act on the body are referred to as "altered drug action." Genetic conditions transmitted as single factors altering the way the body acts on drugs are referred to as "altered drug metabolism". These pharmacogenetic conditions can occur either as rare defects or as polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

As an illustrative embodiment, the activity of drug metabolizing enzymes is a major determinant of both the intensity and duration of drug action: The discovery of genetic polymorphisms of drug metabolizing enzymes (e.g., N-acetyltransferase 2 (NAT 2) and cytochrome P450 enzymes CYP2D6 and CYP2C 19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2CI9 quite frequently experience exaggerated drug response and side effects when they receive standard doses. If a metabolite is the active therapeutic moiety, a PM will show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Thus, the activity of kinase protein, expression of kinase nucleic acid, or mutation content of kinase genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a kinase modulator, such as a modulator identified by one of the exemplary screening assays described herein.

4. Monitoring of Effects During Clinical Trials

Monitoring the influence of agents (e.g., drugs, compounds) on the expression or activity of kinase genes (e.g., the ability to modulate aberrant cell proliferation and/or differentiation) can be applied not only in basic drug screening but also in clinical trials. For example, the effectiveness of an agent, as determined by a screening assay as described herein, to increase or decrease kinase gene expression, protein levels, or protein activity, can be monitored in clinical trials of subjects exhibiting decreased or increased kinase gene expression, protein levels, or protein activity. In such clinical trials, kinase expression or activity and preferably that of other genes that have been implicated in for example, a cellular proliferation disorder, can be used as a marker of cellular growth and differentiation.

For example, and not by way of limitation, genes that are modulated in cells by treatment with an agent (e.g., compound, drug, or small molecule) that modulates kinase activity (e.g., as identified in a screening assay described herein) can be identified. Thus, to study the effect of agents on cellular proliferation disorders, for example, in a clinical trial, cells can be isolated and RNA prepared and analyzed for the levels of expression of kinase genes and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of kinase genes or other genes. In this way, the gene expression pattern can serve as a marker, indicative of the physiological response of the cells to the agent. Accordingly, this response state may be determined before, and at various points during, treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) comprising the steps of (1) obtaining a preadministration sample from a subject prior to administration of the agent; (2) detecting the level of expression of a kinase protein, mRNA, or genomic DNA in the preadministration sample; (3) obtaining one or more postadministration samples from the subject; (4) detecting the level of expression or activity of the kinase protein, mRNA, or genomic DNA in the postadministration samples; (5) comparing the level of expression or activity of the kinase protein, mRNA, or genomic DNA in the preadministration sample with the kinase protein, mRNA, or genomic DNA in the postadministration sample or samples; and (vi) altering the administration of the agent to the subject accordingly to bring about the desired effect, i.e., for example, an increase or a decrease in the expression or activity of a kinase protein.

C. Methods of Treatment

The present invention provides for both prophylactic and therapeutic methods of treating a subject at risk of (or susceptible to) a disorder or having a disorder associated with aberrant kinase expression or activity. Additionally, the compositions of the invention find use in the treatment of disorders described herein, especially viral infections. Treatment is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. "Subject," as used herein, can refer to a mammal, e.g. a human, or to an experimental or animal or disease model. The subject can also be a non-human animal, e.g. a horse, cow, goat, or other domestic animal. A therapeutic agent includes, but is not limited to, small molecules, peptides, antibodies, ribozymes and antisense oligonucleotides.

1. Prophylactic Methods

In one aspect, the invention provides a method for preventing in a subject a disease or condition associated with an aberrant kinase expression or activity by administering to the subject an agent that modulates kinase expression or at least one kinase gene activity. Subjects at risk for a disease that is caused, or contributed to, by aberrant kinase expression or activity can be identified by, for example, any or a combination of diagnostic or prognostic assays as described herein. Administration of a prophylactic agent can occur prior to the manifestation of symptoms characteristic of the kinase aberrancy, such that a disease or disorder is prevented or, alternatively, delayed in its progression. Depending on the type of kinase aberrancy, for example, a kinase agonist or kinase antagonist agent can be used for treating the subject. The appropriate agent can be determined based on screening assays described herein.

2. Therapeutic Methods

Another aspect of the invention pertains to methods of modulating kinase expression or activity for therapeutic purposes. The modulatory method of the invention involves contacting a cell with an agent that modulates one or more of the activities of kinase protein activity associated with the cell. An agent that modulates kinase protein activity can be an agent as described herein, such as a nucleic acid or a protein, a naturally-occurring cognate ligand of a kinase protein, a peptide, a kinase peptidomimetic, or other small molecule. In one embodiment, the agent stimulates one or more of the biological activities of kinase protein. Examples of such stimulatory agents include active kinase protein and a nucleic acid molecule encoding a kinase protein that has been introduced into the cell. In another embodiment, the agent inhibits one or more of the biological activities of kinase protein. Examples of such inhibitory agents include antisense kinase nucleic acid molecules and anti-kinase antibodies.

These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a kinase protein or nucleic acid molecule. In one embodiment, the method involves administering an agent (e.g., an agent identified by a screening assay described herein), or a combination of agents, that modulates (e.g., upregulates or downregulates) kinase expression or activity. In another embodiment, the method involves administering a kinase protein or nucleic acid molecule as therapy to compensate for reduced or aberrant kinase expression or activity.

Stimulation of kinase activity is desirable in situations in which a kinase protein is abnormally downregulated and/or in which increased kinase activity is likely to have a beneficial effect. Conversely, inhibition of kinase activity is desirable in situations in which kinase activity is abnormally upregulated and/or in which decreased kinase activity is likely to have a beneficial effect.

Other Embodiments

In another aspect, the invention features, a method of analyzing a plurality of capture probes. The method can be used, e.g., to analyze gene expression. The method includes: providing a two dimensional array having a plurality of addresses, each address of the plurality being positionally distinguishable from each other address of the plurality, and each address of the plurality having a unique capture probe, e.g., a nucleic acid or peptide sequence; contacting the array with a 14171 protein kinase, preferably purified, nucleic acid, preferably purified, polypeptide, preferably purified, or antibody, and thereby evaluating the plurality of capture probes. Binding, e.g., in the case of a nucleic acid, hybridization with a capture probe at an address of the plurality, is detected, e.g., by signal generated from a label attached to the 14171 protein kinase nucleic acid, polypeptide, or antibody.

The capture probes can be a set of nucleic acids from a selected sample, e.g., a sample of nucleic acids derived from a control or non-stimulated tissue or cell.

The method can include contacting the 14171 protein kinase nucleic acid, polypeptide, or antibody with a first array having a plurality of capture probes and a second array having a different plurality of capture probes. The results of each hybridization can be compared, e.g., to analyze differences in expression between a first and second sample. The first plurality of capture probes can be from a control sample, e.g., a wild type, normal, or non-diseased, non-stimulated, sample, e.g., a biological fluid, tissue, or cell sample. The second plurality of capture probes can be from an experimental sample, e.g., a mutant type, at risk, disease-state or disorder-state, or stimulated, sample, e.g., a biological fluid, tissue, or cell sample.

The plurality of capture probes can be a plurality of nucleic acid probes each of which specifically hybridizes, with an allele of 14171. Such methods can be used to diagnose a subject, e.g., to evaluate risk for a disease or disorder, to evaluate suitability of a selected treatment for a subject, to evaluate whether a subject has a disease or disorder. 14171 is associated with protein kinase activity, thus it is useful for disorders associated with abnormal protein kinase activity.

The method can be used to detect SNPs.

In another aspect, the invention features, a method of analyzing a plurality of probes. The method is useful, e.g., for analyzing gene expression. The method includes: providing a two dimensional array having a plurality of addresses, each address of the plurality being positionally distinguishable from each other address of the plurality having a unique capture probe, e.g., wherein the capture probes are from a cell or subject which express or misexpress 14171 or from a cell or subject in which a 14171 mediated response has been elicited, e.g., by contact of the cell with 14171 nucleic acid or protein, or administration to the cell or subject 14171 nucleic acid or protein; contacting the array with one or more inquiry probe, wherein an inquiry probe can be a nucleic acid, polypeptide, or antibody (which is preferably other than 14171 nucleic acid, polypeptide, or antibody); providing a two dimensional array having a plurality of addresses, each address of the plurality being positionally distinguishable from each other address of the plurality, and each address of the plurality having a unique capture probe, e.g., wherein the capture probes are from a cell or subject which does not express 14171 protein kinase (or does not express as highly as in the case of the 14171 protein kinase positive plurality of capture probes) or from a cell or subject which in which a 14171 protein kinase mediated response has not been elicited (or has been elicited to a lesser extent than in the first sample); contacting the array with one or more inquiry probes (which is preferably other than a 14171 nucleic acid, polypeptide, or antibody), and thereby evaluating the plurality of capture probes. Binding, e.g., in the case of a nucleic acid, hybridization with a capture probe at an address of the plurality, is detected, e.g., by signal generated from a label attached to the nucleic acid, polypeptide, or antibody.

In another aspect, the invention features, a method of analyzing 14171, e.g., analyzing structure, function, or relatedness to other nucleic acid or amino acid sequences. The method includes: providing a 14171 nucleic acid or amino acid sequence; comparing the 14171 sequence with one or more preferably a plurality of sequences from a collection of sequences, e.g., a nucleic acid or protein sequence database; to thereby analyze 14171.

Preferred databases include GenBankTM. The method can include evaluating the sequence identity between a 14171 sequence and a database sequence. The method can be performed by accessing the database at a second site, e.g., over the internet.

In another aspect, the invention features, a set of oligonucleotides, useful, e.g., for identifying SNP's, or identifying specific alleles of 14171. The set includes a plurality of oligonucleotides, each of which has a different nucleotide at an interrogation position, e.g., an SNP or the site of a mutation. In a preferred embodiment, the oligonucleotides of the plurality are identical in sequence with one another (except for differences in length). The oligonucleotides can be provided with different labels, such that an oligonucleotide that hybridizes to one allele provides a signal that is distinguishable from an oligonucleotide that hybridizes to a second allele.

This invention is further illustrated by the following examples that should not be construed as limiting. The contents of all references, patents, and published patent applications cited throughout this application are incorporated herein by reference.

EXPERIMENTAL

EXAMPLE 1

Identification and Characterization of Human 14171 Protein Kinase

The human 14171 protein kinase sequence (FIGS. 1A-1 to 1C, SEQ ID NO:1), which is approximately 3860 nucleotides long including untranslated regions, contains a predicted methionine-initiated coding sequence of about 2355 nucleotides (nucleotides 17–2371 of SEQ ID NO:1; SEQ ID NO:3). The coding sequence encodes a 784 amino acid protein (SEQ ID NO:2).

For general information regarding PFAM identifiers, PS prefix and PF prefix domain identification numbers, refer to Sonnhammer et al. (1997) *Protein* 28:405–420 and http//www.psc.edu/general/software/packages/pfam/pfam.html.

As use herein, the term "protein kinase domain" includes an amino acid sequence of about 200–400 amino acid residues in length and having a bit score for the alignment of the sequence to the protein kinase domain (HMM) of at least 8. Preferably, a protein kinase domain includes at least about 200–300 amino acids, more preferably about 250–300 amino acid residues, and has a bit score for the alignment of the sequence to the protein kinase domain (HMM) of at least 16 or greater. The protein kinase domain (HMM) has been assigned the PFAM Accession PF00069. An alignment of the protein kinase domain (amino acids 22 to 279 of SEQ ID NO:2) of human 14171 protein kinase with a consensus amino acid sequence derived from a hidden Markov model is depicted in FIG. 6.

In a preferred embodiment human 14171 protein kinase-like polypeptide or protein has a "protein kinase domain" or a region which includes at least about 200–400 more preferably about 200–300 or 250–300 amino acid residues and has at least about 60%, 70%, 80%, 90%, 95%, 99%, or 100% sequence identity with an "domain," e.g., the protein kinase domain of human 14171 protein kinase-like polypeptides (e.g., amino acid residues 22 to 279 of SEQ ID NO:2).

As used herein, the term "ankyrin repeat" domain includes an amino acid sequence of about 2–150 amino acid residues in length and having a bit score for the alignment of the sequence to the ankyrin repeat domain (HMM) of at least 8. Preferably, an ankyrin repeat domain includes at least about 5–100 amino acids, more preferably about 5–50 amino acid residues, or about 5–45 amino acids and has a bit score for the alignment of the sequence to the ankyrin repeat domain (HMM) of at least 16 or greater. The ankyrin repeat domain (HMM) has been assigned the PFAM Accession PF00023. The ankyrin repeats are predicted to be between amino acid residues 437–469, 470–502, 503–535, 536–568, 569–602, 603–635; 636–668; 669–701; 702–730; and 734–766 of SEQ ID NO:2.

In a preferred embodiment 14171 protein kinase-like polypeptide or protein has an "ankyrin repeat domain" or a region which includes at least about 2–150 more preferably about 5–100 or 5–50 amino acid residues and has at least about 60%, 70%, 80%, 90%, 95%, 99%, or 100% sequence identity with an "ankyrin repeat domain," e.g., the ankyrin repeat domains of human 14171 (e.g., amino acid residues 437–469, 470–502, 503–535, 536–568, 569–602, 603–635; 636–668; 669–701; 702–730; and 734–766 of SEQ ID NO:2).

To identify the presence of an "protein kinase" or an "ankyrin repeat" domain in a 14171-like protein sequence, and make the determination that a polypeptide or protein of interest has a particular profile, the amino acid sequence of the protein can be searched against a database of HMMs (e.g., the Pfam database, release 2.1) using the default parameters (http://www.sanger.ac.uk/Software/Pfam/HMM_search). For example, the hmmsf program, which is available as part of the HMMER package of search programs, is a family specific default program for MIL-PAT0063 and a score of 15 is the default threshold score for determining a hit. Alternatively, the threshold score for determining a hit can be lowered (e.g., to 8 bits). A description of the Pfam database can be found in Sonhammer et al. (1997) *Proteins* 28(3):405–420 and a detailed description of HMMs can be found, for example, in Gribskov et al. (1990) *Meth. Enzymol.* 183:146–159; Gribskov et al. (1987) *Proc. Natl. Acad. Sci. USA* 84:4355–4358; Krogh et al. (1994) *J. Mol. Biol.* 235:1501–1531; and Stultz et al. (1993) *Protein Sci.* 2:305–314, the contents of which are incorporated herein by reference.

EXAMPLE 2

Tissue Distribution of 14171 Protein Kinase mRNA

Figure 5:
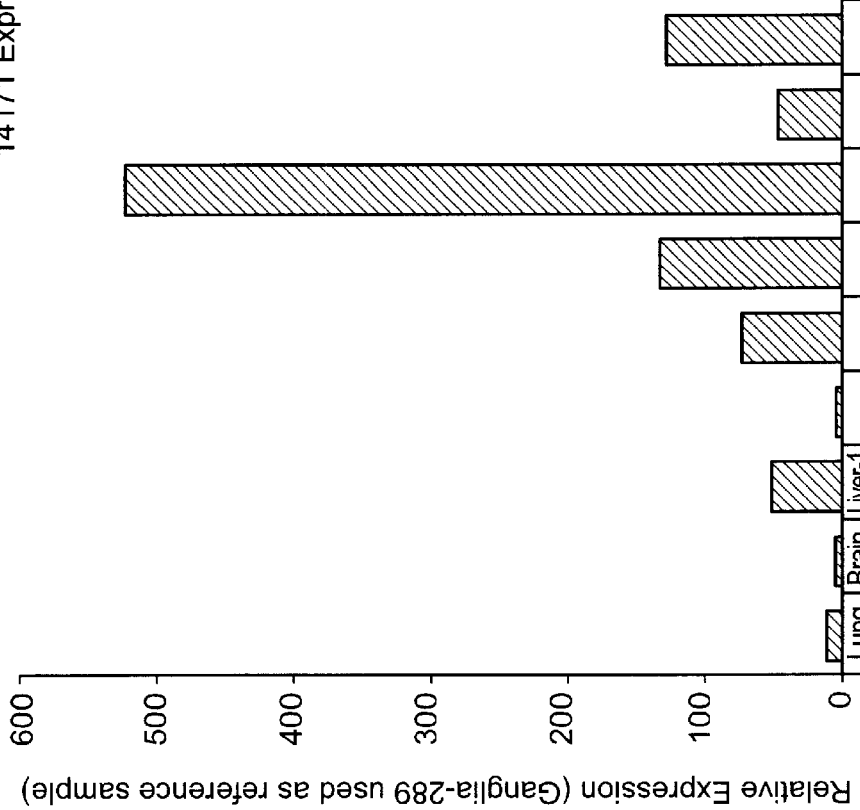
FIG. 5 shows expression of 14171 in HepG2 (immortalized human hepatocyte) cells and elevated expression in HepG2.2.15 (HepG2 stably transfected with a HBV genome) cells.

Expression levels of 14171 in various tissues and cell lines were determined by quantitative RT-PCR (Taqman® brand quantitative PCR kit, Applied Biosystems). The quantitative RT-PCR reactions were performed according to the kit manufacturer's instructions. The results are shown in FIG. 5.

Northern blot hybridizations with various RNA samples are performed under standard conditions and washed under stringent conditions, i.e., 0.2×SSC at 65° C. A DNA probe corresponding to all or a portion of the 14171 cDNA (SEQ ID NO:3) can be used. The DNA is radioactively labeled with $^{32}$P-dCTP using the Prime-It Kit (Stratagene, La Jolla, Calif.) according to the instructions of the supplier. Filters containing mRNA from mouse hematopoietic and endocrine tissues, and cancer cell lines (Clontech, Palo Alto, Calif.) are probed in ExpressHyb hybridization solution (Clontech) and washed at high stringency according to manufacturer's recommendations.

RNA was isolated from HepG2 (immortalized human hepatocyte cells) and HepG2.2.15 (HepG2 stably transfected with the HBV genome). 14171 RNA is more abundant in HBV-infected HepG2 cells than in uninfected HepG2 cells.

EXAMPLE 3

Recombinant Expression of 14171 in Bacterial Cells

In this example, 14171 is expressed as a recombinant glutathione-S-transferase (GST) fusion polypeptide in *E. coli* and the fusion polypeptide is isolated and characterized. Specifically, 14171 is fused to GST and this fusion polypeptide is expressed in *E. coli*, e.g., strain PEB 199. Expression of the GST-14171 fusion protein in PEB 199 is induced with IPTG. The recombinant fusion polypeptide is purified from crude bacterial lysates of the induced PEB 199 strain by affinity chromatography on glutathione beads. Using polyacrylamide gel electrophoretic analysis of the polypeptide purified from the bacterial lysates, the molecular weight of the resultant fusion polypeptide is determined.

EXAMPLE 4

Expression of Recombinant 14171 Protein in COS Cells

To express the 14171 gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire 14171 protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the 14171 DNA sequence is amplified by PCR using two primers. The 5' primer contains the restriction site of interest followed by approximately twenty nucleotides of the 14171 coding sequence starting from the initiation codon; the 3' end sequence contains complementary sequences to the other restriction site of interest, a translation stop codon, the HA tag or FLAG tag and the last nucleotides of the 14171 coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the 14171 gene is inserted in the correct orientation. The ligation mixture is transformed into *E. coli* cells (strains HB101, DH5α, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the 14171-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning. A Laboratory Manual.* 2nd, ed., Cold Spring Harbor Laboratory, Cold Spring Harbor Laboratory Press, Cold Spring Harbor, N.Y., 1989. The expression of the 14171 polypeptide is detected by radiolabelling ($^{35}$S-methionine or $^{35}$S-cysteine available from NEN, Boston, Mass., can be used) and immunoprecipitation (Harlow, E. and Lane, D. *Antibodies: A Laboratory Manual*, Cold Spring Harbor Laboratory Press, Cold Spring Harbor, N.Y., 1988) using an HA specific monoclonal antibody. Briefly, the cells are labeled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the 14171 coding sequence is cloned directly into the polylinker of the pCDNA/Amp vector using the appropriate restriction sites. The resulting plasmid is transfected into COS cells in the manner described above, and the expression of the 14171 polypeptide is detected by radiolabelling and immunoprecipitation using a 14171 specific monoclonal antibody.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

Those skilled in the art will recognize, or be able to ascertain using no more than routine experimentation, many equivalents to the specific embodiments of the invention described herein. Such equivalents are intended to be encompassed by the following claims.

That which is claimed:

1. An isolated nucleic acid molecule selected from the group consisting of:
   a) a nucleic acid molecule comprising a nucleotide sequence of SEQ ID NO:1, SEQ ID NO:3, or a complement thereof; and
   b) a nucleic acid molecule which encodes a polypeptide comprising the amino acid sequence of SEQ ID NO:2.

2. An isolated nucleic acid molecule which encodes a polypeptide comprising the amino acid sequence of SEQ ID NO:2, wherein the polypeptide has a stibstitudon for aspartate at position 143.

3. The nucleic acid molecule of claim 1 further comprising nucleic acid sequences encoding a heterologous polypeptide.

4. An isolated nucleic acid molecule of claim 1, wherein the nucleic acid molecule comprises a nucleotide sequence of SEUQ ID NO:1, SEQ ID NO:3, or a complement thereof.

5. An isolated nucleic acid molecule of claim 1, wherein the nucleic acid molecule comprises a nucleic acid molecule which encodes a polypeptide comprsing the amino acid sequence of SEQ ID NO:2.

6. A vector comprising the nucleic acid molecule of claim 1.

7. A vector comprising the nucleic acid molecule of claim 2.

8. The vector of claim 6 further comprising a nucleic acid sequence which regulates expression of the nucleic acid molecule.

9. The vector of claim 7 further comprising a nucleic acid sequence which regulates expression of the nucleic acid molecule.

10. A host cell comprising the vector of claim 6.

11. A host cell comprising the vector of claim 7.

12. The host cell of claim 10 which is a mammalian host cell.

13. The host cell of claim 11 which is a mammalian host cell.

14. A method of producing a polypeptide comprising: culturing the host cell of claim 10 under conditions in which the nucleic acid molecule is expressed to produce said polypeptide.

15. A method of producing a polypeptide comprising: culturing the host cell of claim 11 under conditions in which the nucleic acid molecule is expressed to produce said polypeptide.

* * * * *